(12) United States Patent
Sarhan et al.

(10) Patent No.: US 10,641,734 B2
(45) Date of Patent: May 5, 2020

(54) MICRO POWERED ULTRA-HIGH RESOLUTION ELECTROMAGNETIC SENSOR WITH REAL TIME ANALOG CIRCUITRY BASED ARTIFACT CANCELLATION

(71) Applicants: Sameh Sarhan, Santa Clara, CA (US); Lawrence Herbert Zuckerman, Livermore, CA (US)

(72) Inventors: Sameh Sarhan, Santa Clara, CA (US); Lawrence Herbert Zuckerman, Livermore, CA (US)

(73) Assignee: Xtrava Inc., Santa Clara, CA (US)

( * ) Notice: Subject to any disclaimer, the term of this patent is extended or adjusted under 35 U.S.C. 154(b) by 0 days.

(21) Appl. No.: 15/687,478

(22) Filed: Aug. 27, 2017

(65) Prior Publication Data

US 2018/0059059 A1    Mar. 1, 2018

Related U.S. Application Data

(60) Provisional application No. 62/380,421, filed on Aug. 28, 2016.

(51) Int. Cl.
| | | |
|---|---|---|
| *G01N 27/72* | (2006.01) | |
| *A61B 5/05* | (2006.01) | |
| *A61B 5/00* | (2006.01) | |
| *A61B 5/04* | (2006.01) | |

(52) U.S. Cl.
CPC ......... *G01N 27/72* (2013.01); *A61B 5/04005* (2013.01); *A61B 5/05* (2013.01); *A61B 5/6804* (2013.01); *A61B 5/7214* (2013.01); *A61B 2562/0223* (2013.01)

(58) Field of Classification Search
CPC ...................................................... G01N 27/72
USPC ............................................................ 324/243
See application file for complete search history.

(56) References Cited

U.S. PATENT DOCUMENTS

| | | | | |
|---|---|---|---|---|
| 2008/0234534 A1* | 9/2008 | Mikas | ...................... | A61N 2/02 600/14 |
| 2009/0306524 A1* | 12/2009 | Muhlsteff | .............. | A61B 5/021 600/485 |
| 2011/0190849 A1* | 8/2011 | Faltys | ................ | A61N 1/36053 607/50 |
| 2011/0263925 A1* | 10/2011 | Bratton | .................. | A61N 2/004 600/14 |
| 2013/0303924 A1* | 11/2013 | Rosell Ferrer | ....... | A61B 5/0522 600/508 |
| 2013/0314081 A1* | 11/2013 | Igney | ................... | G01N 27/023 324/239 |
| 2015/0065841 A1* | 3/2015 | Lee | ........................ | A61B 5/053 600/388 |
| 2015/0065842 A1* | 3/2015 | Lee | .................... | A61B 5/04085 600/388 |
| 2018/0143150 A1* | 5/2018 | Bezemer | ................ | A61B 5/721 |

* cited by examiner

*Primary Examiner* — Jason C Olson

(57) ABSTRACT

An ultra-miniature and micro-powered system, apparatus, and method utilizing electromagnetic imaging via minute eddy currents, analog circuit averaging and artifact cancellation, that attaches to the outside of clothing and measures internal bodily functions including but not limited to heart rate, respiration rate, and wetness of underclothing.

15 Claims, 22 Drawing Sheets

MICRO POWERED ULTRA-HIGH RESOLUTION ELECTROMAGNETIC SENSOR WITH REAL TIME ANALOG CIRCUITRY BASED ARTIFACT CANCELLATION

TECHNICAL FIELD

This disclosure relates generally to eddy current measurement instruments, electromagnetic imaging, and signal cancellation techniques. This disclosure relates to contactless measurements of material properties, and distance and orientation of objects, when eddy currents are induced in them by locally generated AC magnetic fields. This disclosure further relates to non-invasive measurement of internal bodily properties and functions, detected by effects on the impedance of a very high Q parallel tuned circuit energized with extremely low power alternating currents in the 2 MHz to 20 MHz frequency range. More specifically, this disclosure relates to the use of sensors in addition to eddy current probes that respond to each source of unwanted measurement artifact. The analog signal from each artifact sensor, properly scaled, is used to offset the instantaneous eddy current measurement to cancel its artifact.

BACKGROUND

It is often the case that when an intended measurement is being made, the sensing device also responds to unintended physical variables or properties. For instance, a strain gauge instrument may be applied to determine the weight bearing on a mechanical member, but if the instrument is not designed properly, it may also be measuring the mechanical member's temperature. In some situations, such as with incremental measurements or time aspects being measured, the intended measurement can be separated from unintended measurement, because the time scales differ. For the above example, temperature changes may take place on a scale of hours, whereas relevant weight-bearing load changes may occur on a scale of seconds. In this case, the relevant weight-bearing load measurements could be changes in load as opposed to absolute values and/or frequency and/or other time patterns of these changes.

If the effects cannot be separated by time scale or frequency spectrum, additional sensors can be added that measure only the unintended variable. For the above example, the temperature response of the strain gauge instrument can be determined, and a temperature sensor can be added to determine the true weight bearing load, regardless of temperature changes.

For some years, there have appeared on the market a large number of products that monitor vital signs to track disease states. More recently, there has been a shift in emphasis to monitor the vital signs of individuals for whom there is no suspected illness, but for early indications of health problems. Examples of such vital signs are heart rate and motion, blood pressure, and respiration rate. Part of the need is to provide measurements for a period of hours that may span a variety of activities, such as relaxation, physical exercise, and stressful mental activities. Such measurements can be recorded automatically for later analysis, and in some cases, even be accompanied by alarms when there are readings that do not fall within selected limits.

Also, during the past several years, there have been many products introduced to allow monitoring of infants and others for reasons of safety. Parents and others are able to monitor subjects who are located in different rooms of a dwelling or in completely different locations.

BRIEF SUMMARY

This Brief Summary is provided as a general introduction to the Disclosure provided by the Detailed Description and Figures, summarizing some aspects of the disclosed invention. It is not a detailed overview of the Disclosure, and should not be interpreted as identifying key elements of the invention, or otherwise characterizing the scope of the invention disclosed in this Patent Document.

Reference is made to U.S. application Ser. No. 15/082,638, filed 28 Mar. 2016, which is itself cross referenced to U.S. Provisional Application 62/141,272 filed 1 Apr. 2015). That application contains technical details to further support the instant application and is incorporated to the instant application by reference.

The instant disclosure teaches methods to improve the quality and accuracy of minute eddy current measurements of internal bodily organs and functions. This includes methods to focus on particular small useful loss ranges extracted from a very large eddy current loss range. It is also shown how to separate desired measurements of bodily functions using eddy current probe sensor technology from unwanted measurements that are also captured by the same sensor, such as motion of clothing relative to a Subject's body. A related subject of the instant disclosure is to implement the above methods using low power and high speed analog circuitry instead of digital circuitry, for various advantages including reduced power consumption.

Other aspects, features and advantages of the invention will be apparent to those skilled in the art from the following Disclosure.

BRIEF DESCRIPTION OF DRAWINGS

For a more complete understanding of this disclosure and its features, reference is now made to the following description, taken in conjunction with the accompanying drawings, in which.

DETAILED DESCRIPTION

The various figures, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

In general, this disclosure provides a means to use the outputs of a variety of sensors to distinguish between desired effects being measured and undesired effects being measured-here termed "artifacts"—of a particular sensor or measurement device. Such means may be applied in real time and may utilize analog circuitry for low cost, size and power consumption. This disclosure also provides a means for zeroing in on particular small ranges of the measured variable, which has a total range spanning multiple orders of magnitude.

Depending on the implementation, these techniques can provide significant benefits in a range of fields, such as instruments that measure physical variables.

Figure 1:
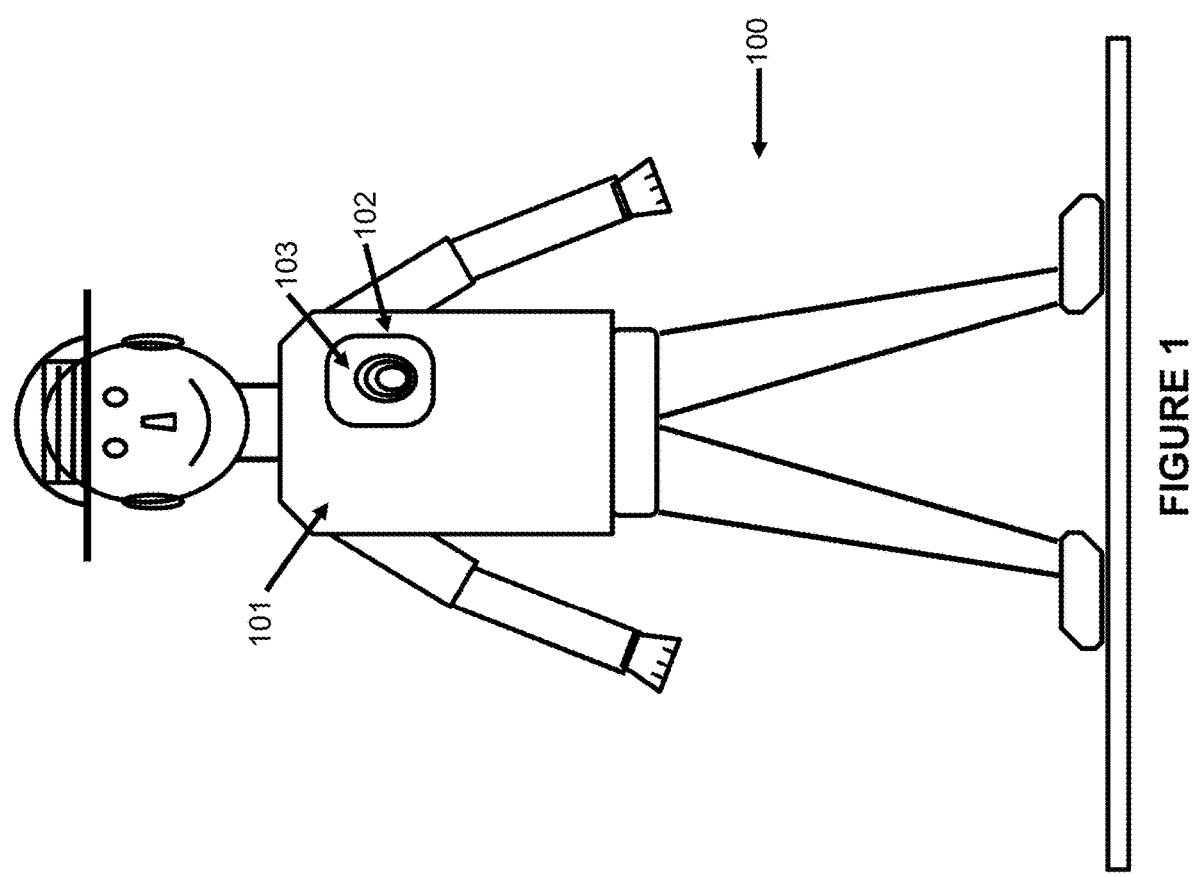
FIG. 1 illustrates a basic wearable electromagnetic sensor configuration.

FIG. 1 illustrates a basic wearable configuration 100. The person ("Subject") is wearing an undergarment 101, with a thin, low power electronic "patch" or other suitable assembly 102 that includes a high Q flat coil inductor 103. Assembly 102 is smaller, relative to the size of the subject, than the one shown in the figure. Not shown in the figure are any over-garments that cover the undergarment 101 and assembly 102, allowing the latter to be comfortable and unobtrusive. Inductor 103 is part of a tuned circuit probe that is in turn part of an eddy current measuring circuit. Assembly 102 could be attached to clothing on any part of the body, including, for instance, to the outside of a diaper.

In addition to an eddy current measuring device, assembly 102 could contain a variety of sensors and signal processing circuits. It could continuously measure heart rate, respiration rate, and other biophysical variables. It could also measure the Subject's motions and other physical activities. It could sense the Subject's environment, such as sound, temperature, and radiation. The Subject could be standing, as shown in the figure, or walking, running, climbing, sitting, lying down, eating, drinking, excreting, or sleeping.

Assembly 102 could communicate this data to a smart phone worn by the subject or to some other assembly close to the Subject, either of which could, in turn, send the data anywhere, near or far, including to a different room, a hospital, or ambulance station. Such communication could use existing infrastructure as necessary. The data recipient could, for instances, be a family member, a caregiver, or a medical professional.

Figure 2:
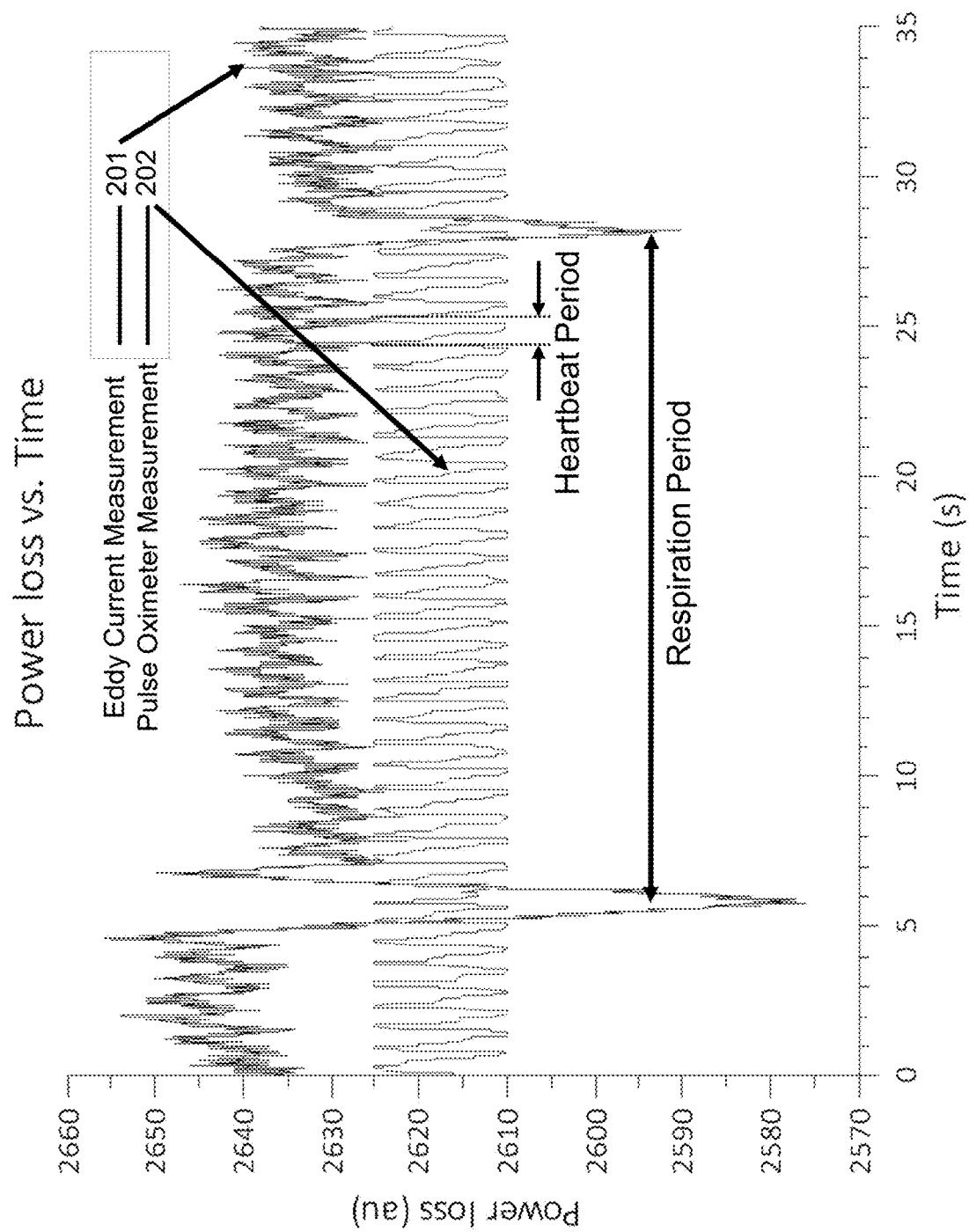
FIG. 2 shows example heart rate and respiration rate data obtained using apparatus depicted in FIG. 1.

FIG. 2 shows example data obtained by the inventors using apparatus depicted in FIG. 1 and described in one or more of the embodiments. The lower trace 202, heartbeat rate data from a pulse oximeter, does not belong on this graph but is shown superimposed for comparison. The upper trace 201 is the eddy current data showing heart and respiration rate. The vertical, "power loss" scale shows relative units of power lost in the inductor 103, corresponding to the minute amount of power dissipation through eddy currents within the Subject. The data shown is prior to filtering. Respiration and heartbeat (pulse) period are clearly distinguished.

Owing to the substantial time scale difference between heart rate and respiration rate, it is easy to distinguish between the two measurement variables through use of filtering, even though the eddy current measurement is sensitive to both.

Figure 3:
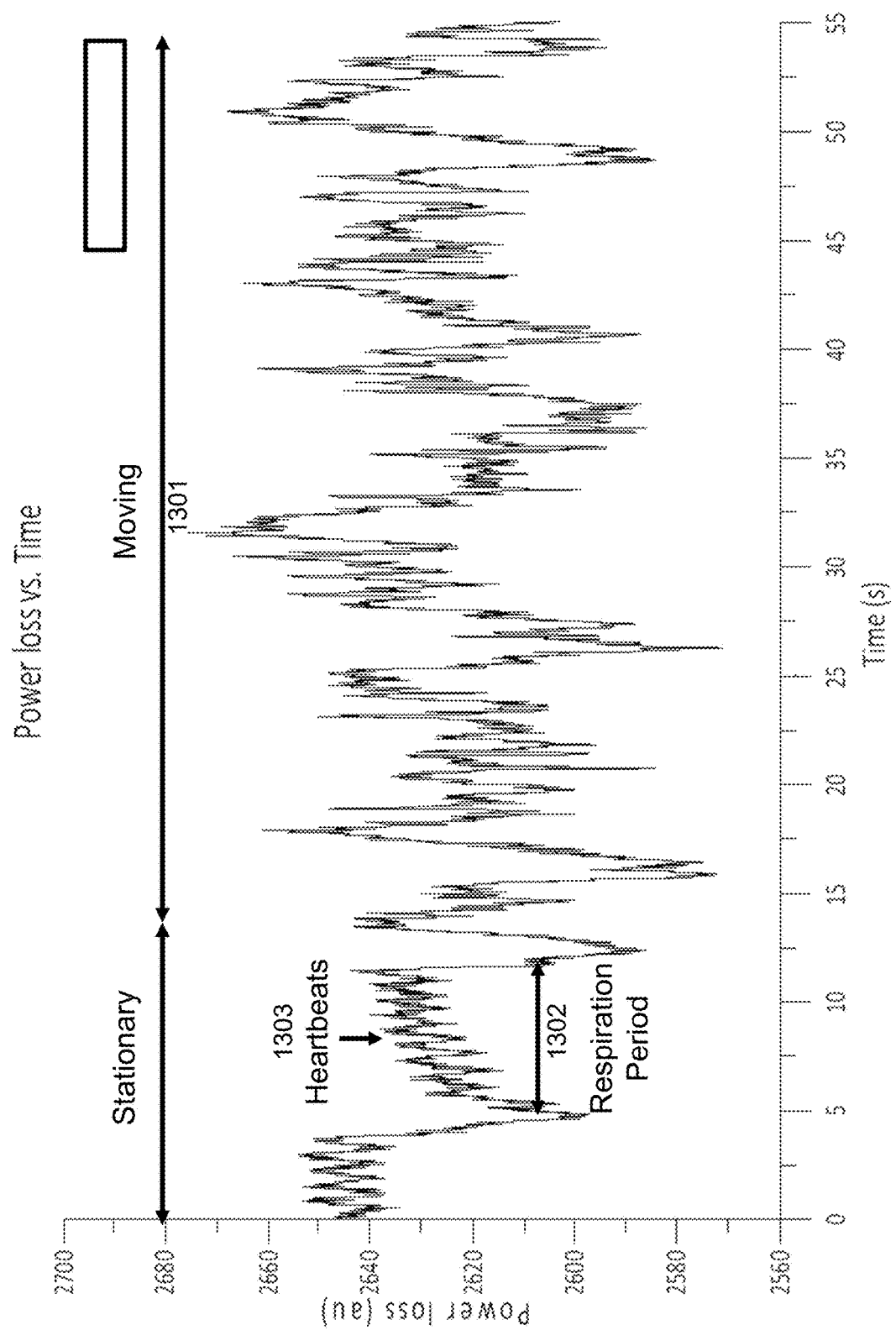
FIG. 3 shows comparison of heart and respiration rate data, obtained from equipment represented in FIG. 1, where the subject is first stationary then moving, and for which no filtering, machine learning, or other data improvement techniques are used.

FIG. 3 shows comparison of heart and respiration rate data, obtained from equipment represented in FIG. 1, where the subject is first stationary then moving, and for which no filtering, machine learning, or other data improvement techniques are used. This figure shows the effects of a motion artifact; data from the instrument is subject to severe interference when the Subject is moving, 1301. As shown, the respiration data, 1302 is severely degraded, and the heart rate data 1303 appears to be almost completely obscured.

Figure 4:
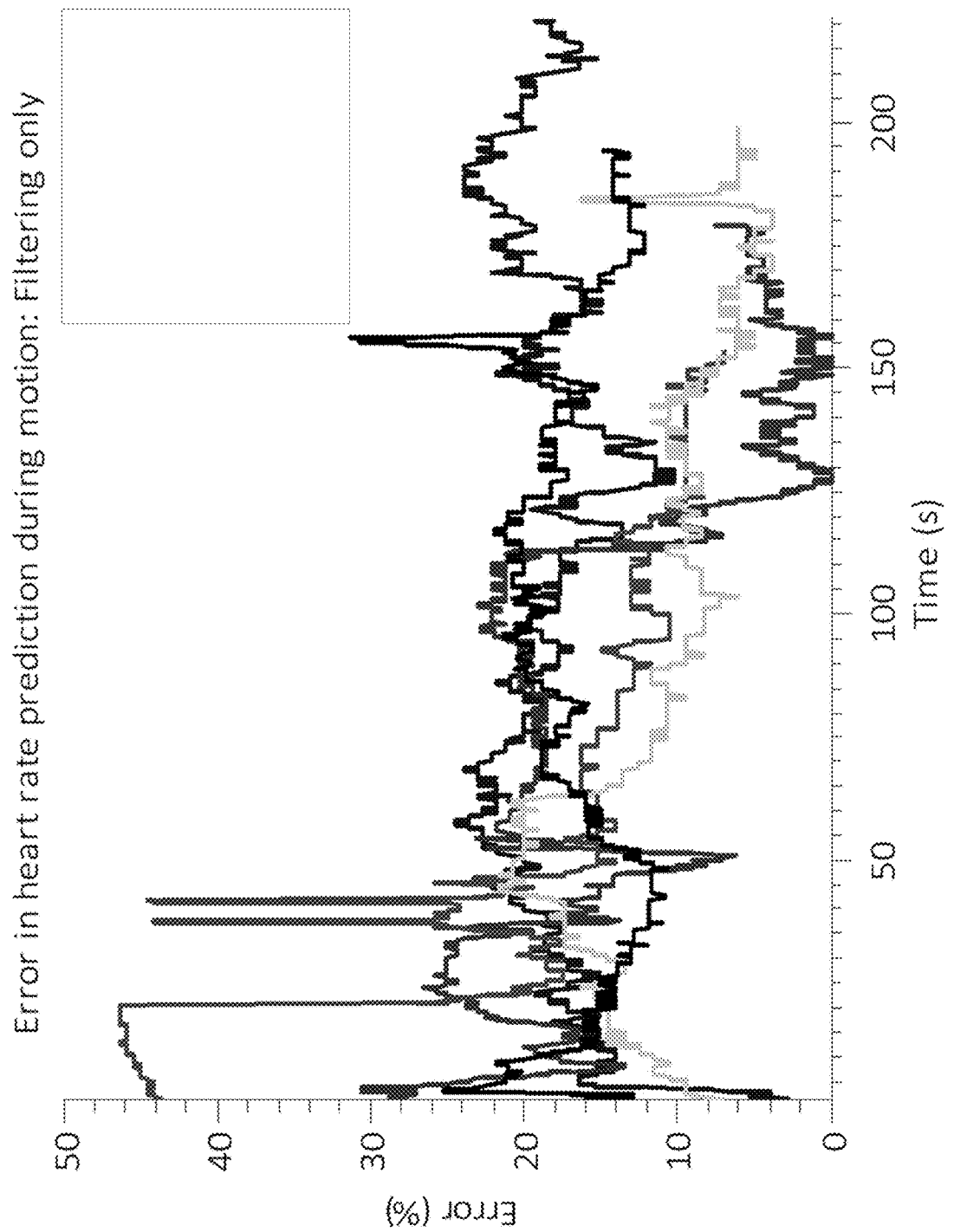
FIG. 4 shows heart and respiration rate data from equipment represented in FIG. 1, where the subject is in motion and for which signal filtering is used.

FIG. 4 shows heart and respiration rate data from equipment represented in FIG. 1, where the subject is in motion and for which signal filtering is used. A small study was performed that reports cumulative heart rate measurement error rate over a period of 200 seconds for five subjects. One might expect that even with noisy data, the cumulative error rate would gradually diminish, as there are an increasing number of samples to average. As shown, however, the noise from the motion artifact is generally not Gaussian; the trend is down for only three of the subjects. The overall absolute value error is about 20%.

Figure 5:
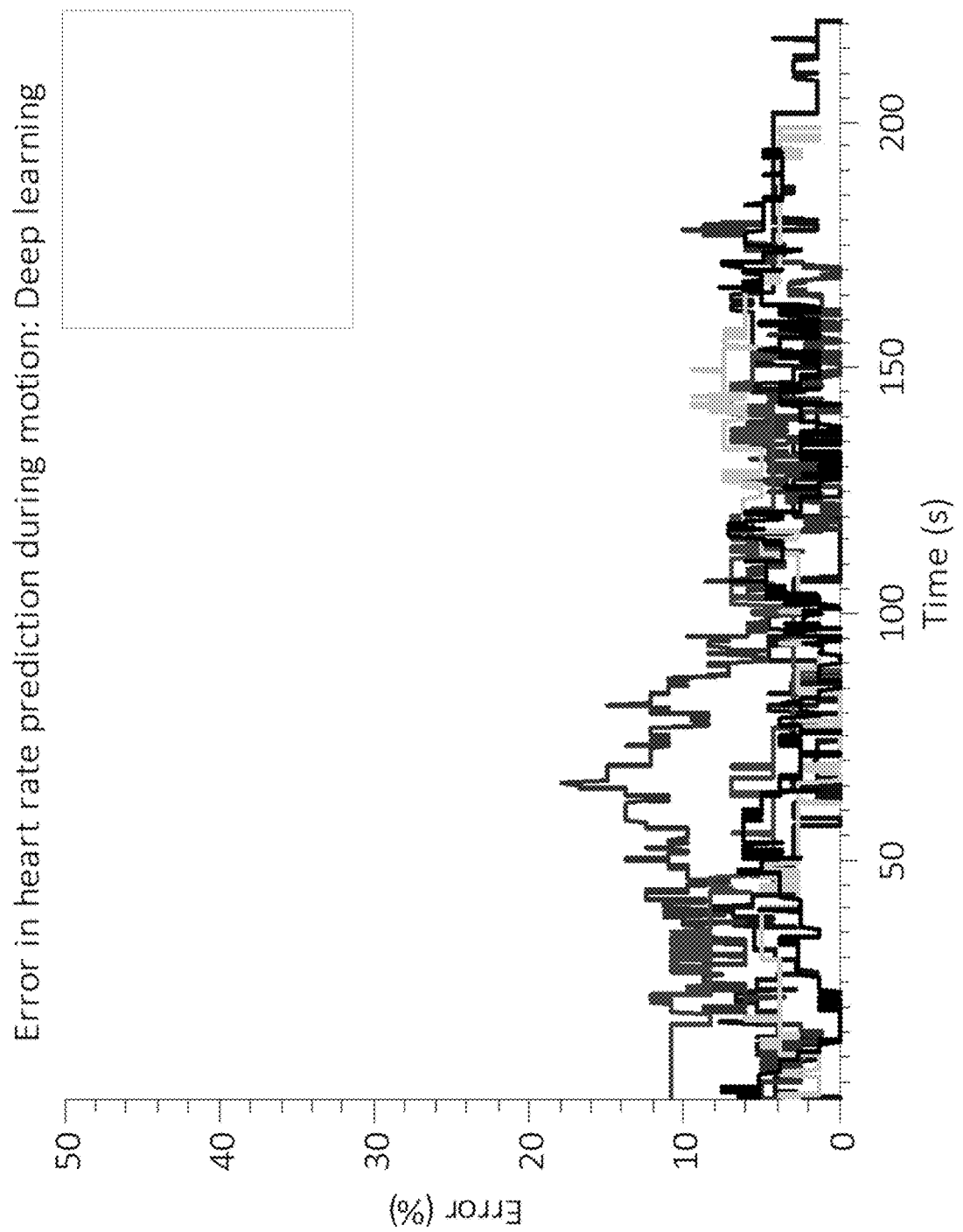
FIG. 5 shows similar heart and respiration rate data from equipment represented in FIG. 1, where the subject is in motion and for which signal filtering plus deep machine learning has been applied.

FIG. 5 shows similar heart and respiration rate data from equipment represented in FIG. 1, where the subject is in motion and for which signal filtering plus deep machine learning has been applied. The improvement is pronounced, with error generally well under 5%, which may be clinically acceptable.

Although filtering, and especially deep machine learning resulted in a pronounced error reduction, an even lower error rate may be needed. Moreover, deep machine learning may not have the required speed for critical real time data, and its power requirement may preclude its implementation in ultra-compact and minimal weight wearable instruments. Even if this digital processing is performed within a mobile telephone or other equipment on the Subject's person or by equipment located nearby, the communication rate may be too much of a battery power burden for the wearable instrument, such as in FIG. 1. Clearly, an additional method of separating desired and undesired physical effects would be useful.

Figure 6:
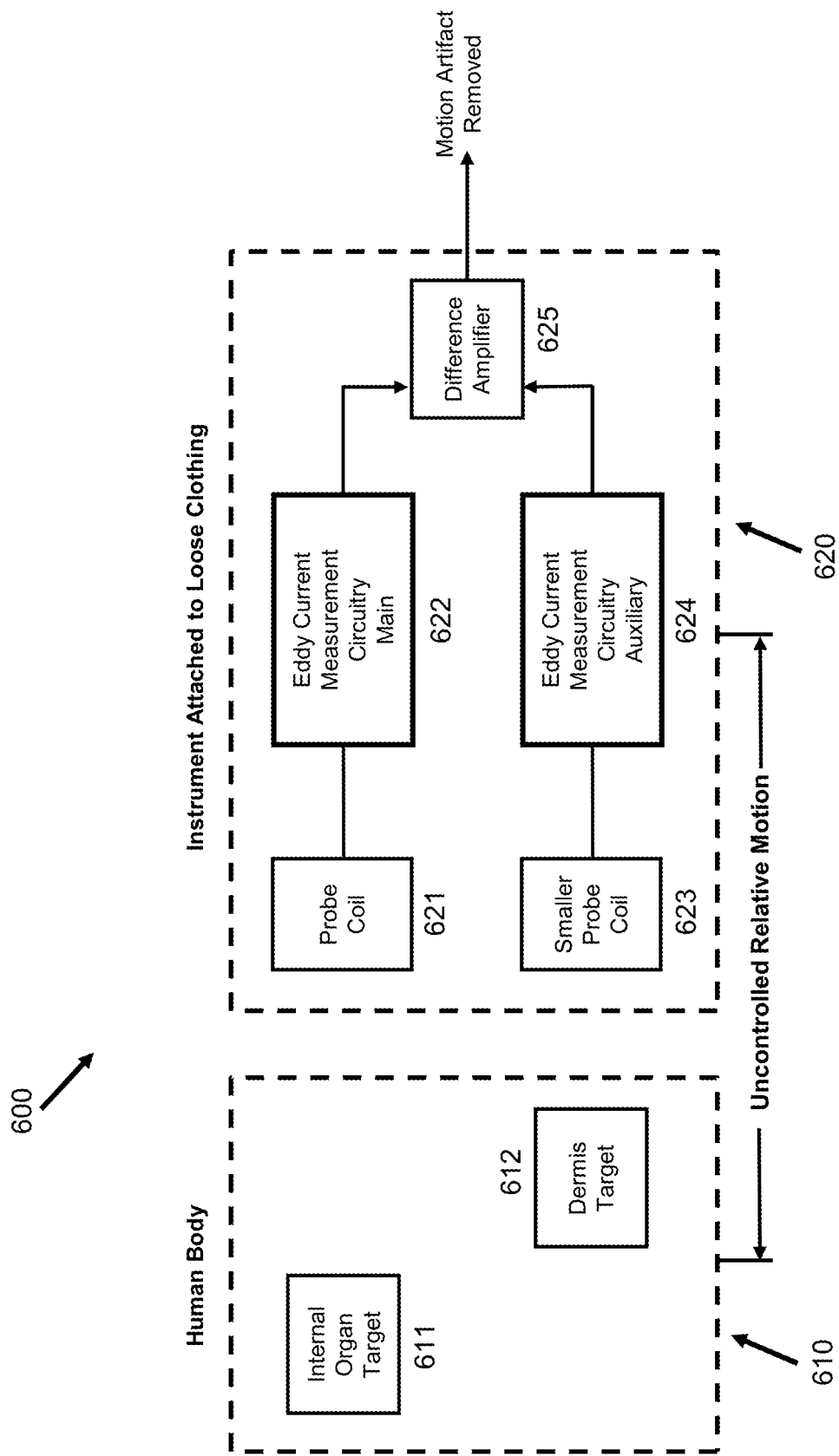
FIG. 6 shows a basic idea to remove or reduce the level of an unwanted measurement artifact, such as from motion.

FIG. 6 shows a basic idea to remove or reduce the level of an unwanted measurement artifact. Block 610 represents the human body, and Block 620 represents a dual eddy current instrument that may be attached to loose clothing. In this case, the desired eddy current measurement is the motion of an internal organ 611 or a fluid such as blood. Motion of blood into and out of the heart represents an eddy current instrument target with periodic changing conductance. The Main Eddy Current Probe Coil 621 with Circuitry 622 are also sensitive to relative motion between the body and the clothing to which they are attached. The eddy current loss in probe coil 621 increases and decreases as the clothing approaches and recedes from human body 610, which could obscure the internal organ 611 signal. The relative motion artifact is the signal seen in the "Moving" portion of FIG. 3.

The Auxiliary Eddy Current Circuitry 624 uses a smaller probe coil 623, whose magnetic field does not reach the internal organs, only the outer body layers, such as the dermis. Therefore, its output signal contains only the relative motion signal. When the Main and Auxiliary signals are combined in difference amplifier 625, the motion artifact is cancelled.

Figure 7:
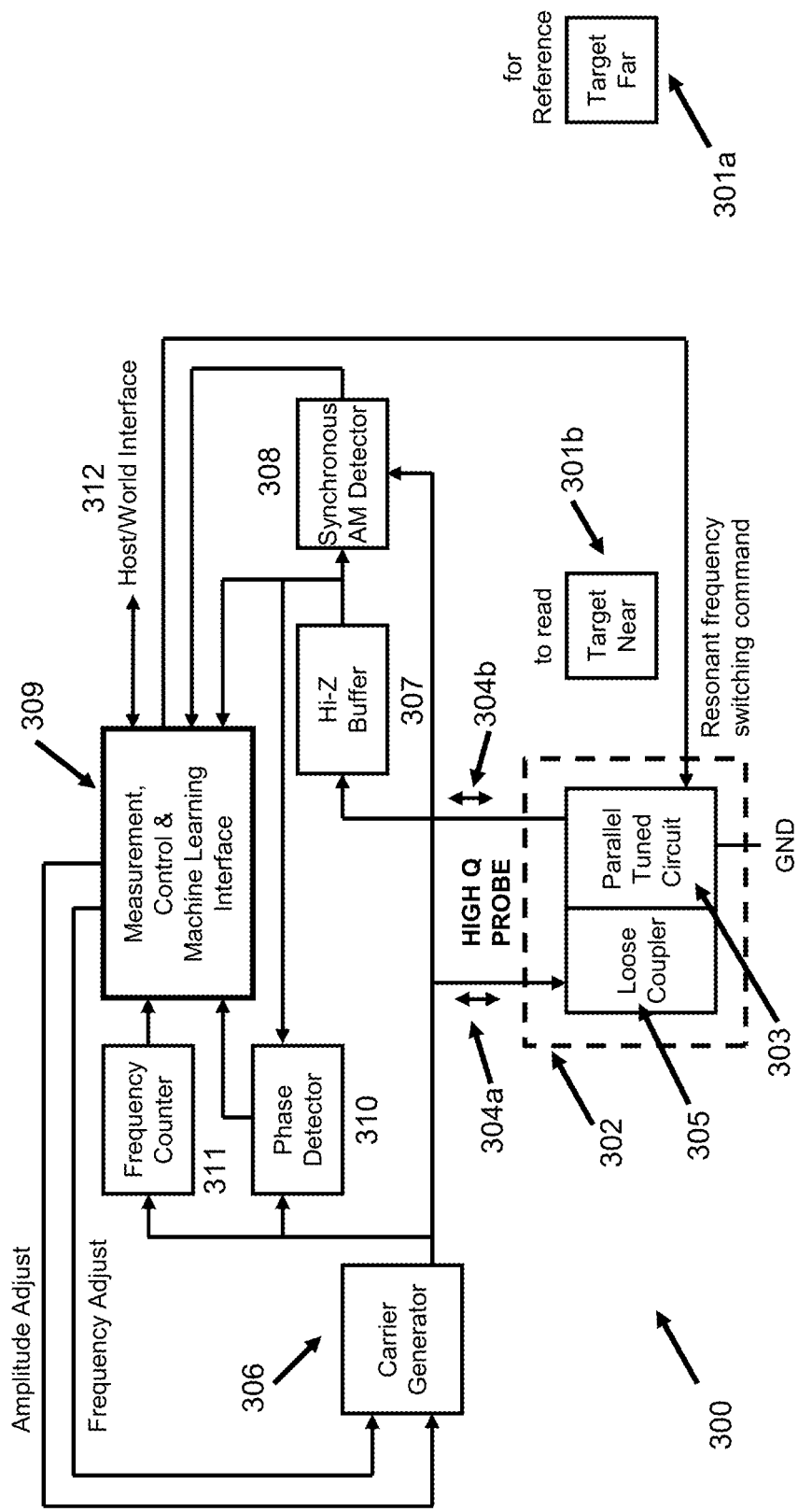
FIG. 7 shows an embodiment of an eddy current instrument wherein the eddy current probe tuned circuit is not part of an oscillator circuit but rather is driven by a frequency and amplitude agile carrier source).
Figure 8:
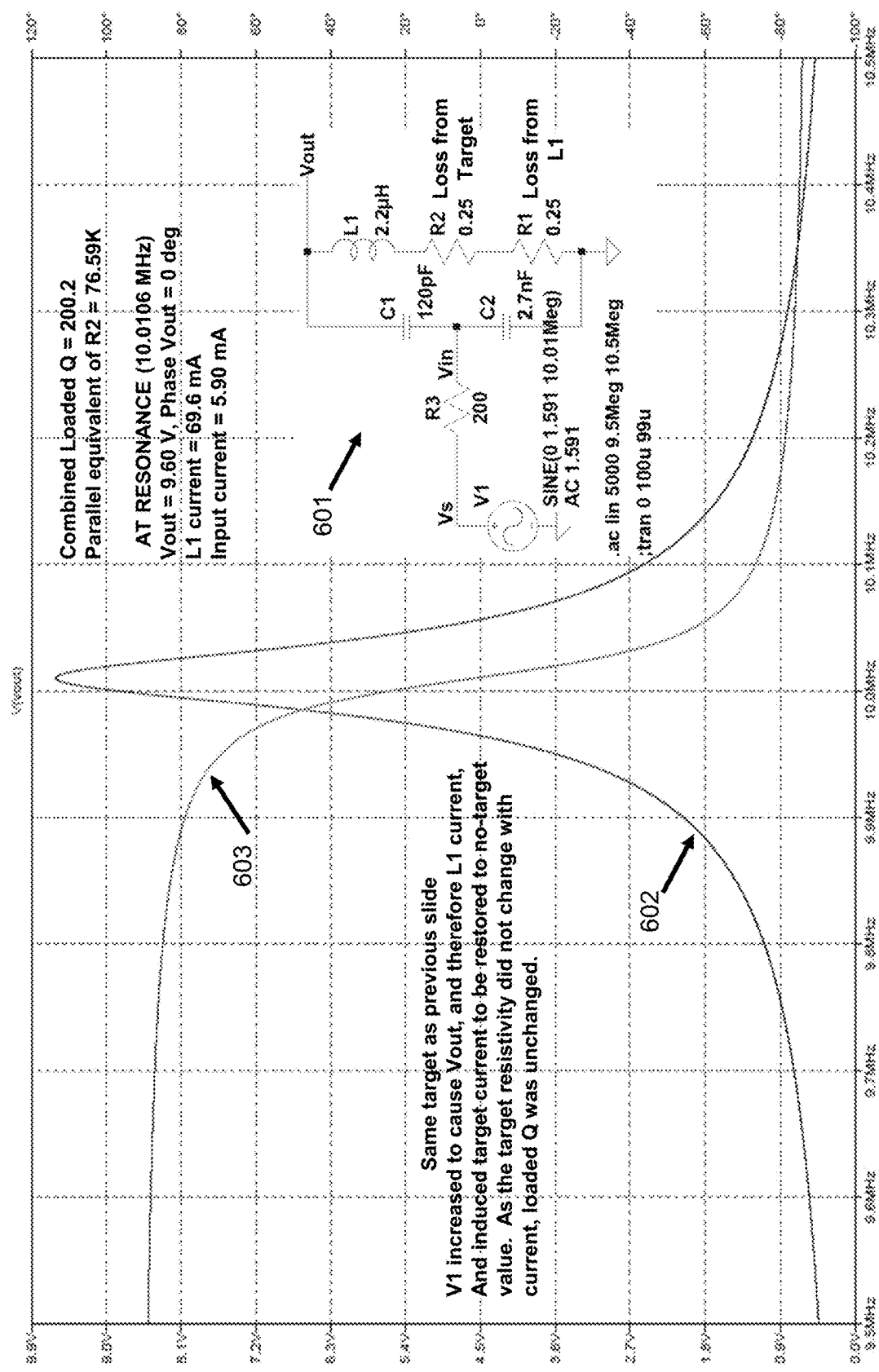
FIG. 8 shows the response of the probe parallel tuned circuit block in FIG. 7, located near a very low loss eddy current target.
Figure 9:
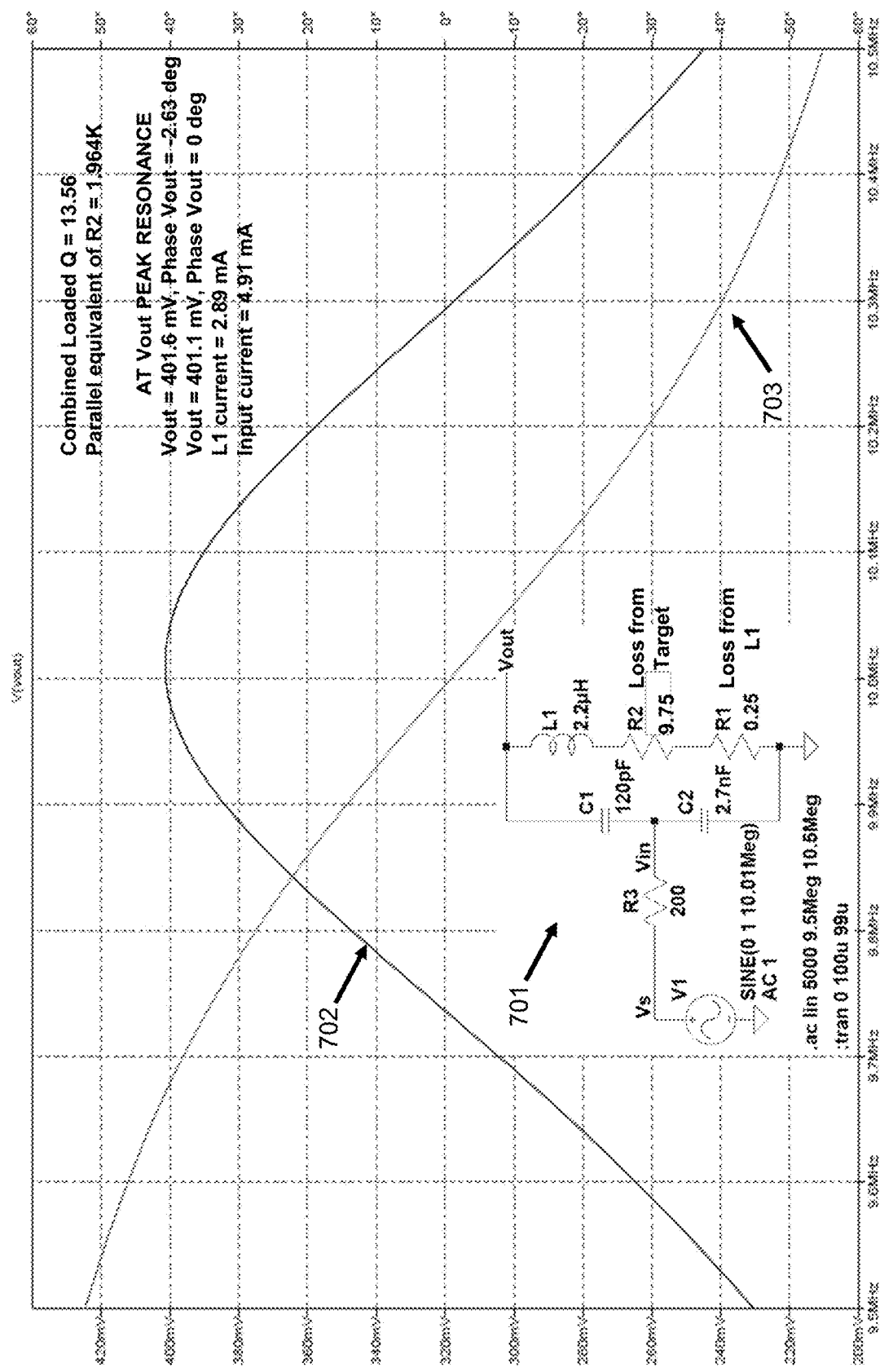
FIG. 9 shows the response of the same probe parallel tuned circuit block in FIG. 7, located near a relatively high loss eddy current target.

FIG. 7 is a copy of FIG. 3 of U.S. application Ser. No. 15/082,638, filed 28 Mar. 2016, where it is described in great detail. It shows an embodiment of an eddy current instrument wherein the eddy current probe tuned circuit 303 is not part of an oscillator circuit but rather is driven by a frequency and amplitude agile carrier source (306). FIG. 8 is a copy of FIG. 6 of that same application. It shows the response of this probe parallel tuned circuit for a very low loss target, as represented by a very small resistance R2 in series with probe coil L1. FIG. 9 is a copy of FIG. 7 of that same patent application. It shows the response of the same probe parallel tuned circuit, 303 in FIG. 7, but in the vicinity of a relatively high loss target, as represented by a larger resistance R2 in series with probe coil L1. It should be noted that the eddy current target losses, instead of R2, can equally well be represented by resistances of suitable values in parallel with the probe tuned circuit, such as between Vout and ground. In that case, the designation "Rp" is often used.

As further explained in U.S. application Ser. No. 15/082,638, filed 28 Mar. 2016, the curves in FIGS. 8 and 9 illustrate the commonly known fact that increased loss results in a broadening of the resonance curve, quantified by decreased tuned circuit Quality Factor ("Q"). Additional effects of increased loss are decreased tuned circuit output voltage Vout, and decreased circulating current. It should be emphasized that these losses, even though represented by R2, actually occur within the eddy current targets.

Figure 10:
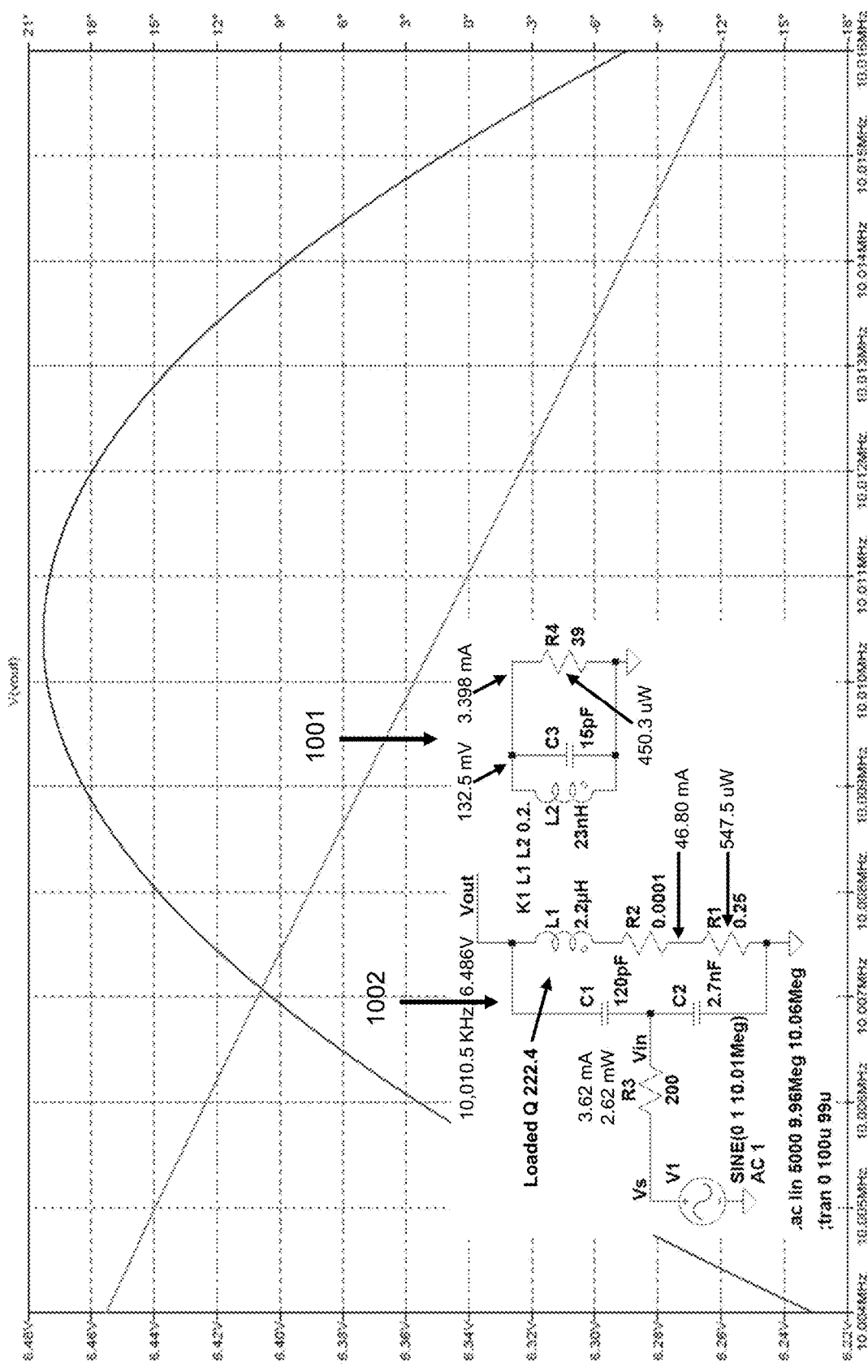
FIG. 10 shows the response of the same probe parallel tuned circuit block in FIG. 7 located near a relatively high loss eddy current target, where the target simulation more closely represents the actual physical configuration
Figure 11:
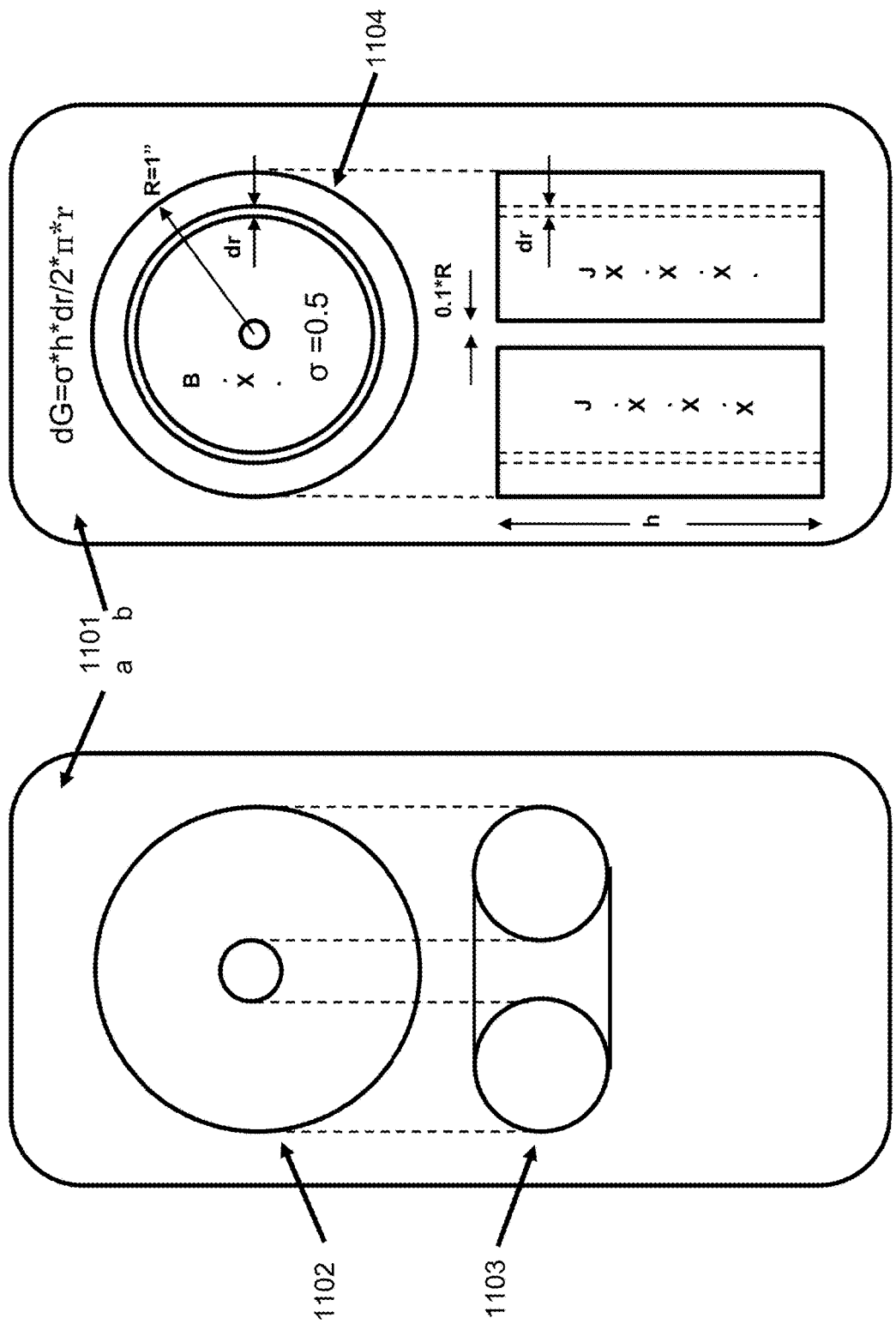
FIG. 11 depicts within a target conductance, current density, and magnetic field estimates diagrammatically, that can be used to derive the equivalent circuit ("sub-circuit") values shown in FIG. 10.

FIG. 10 is a copy of FIG. 10 of that same patent application. Here, instead of representing a significant target load by a resistor within the probe tuned circuit, it is represented more closely to the physical situation within a Subject's body, where the tissues, organs, or fluids may have electrical characteristics with the equivalent circuit values L2, R4, and C3. Magnetic coupling between the probe and target tuned circuits is represented by mutual coupling coefficient K1. FIG. 11 is a copy of FIG. 11 of that same patent application. It depicts something about magnitude and direction of currents and fields within the body. The text in said patent application derives probable values for the constants in FIG. 10.

Figure 12:
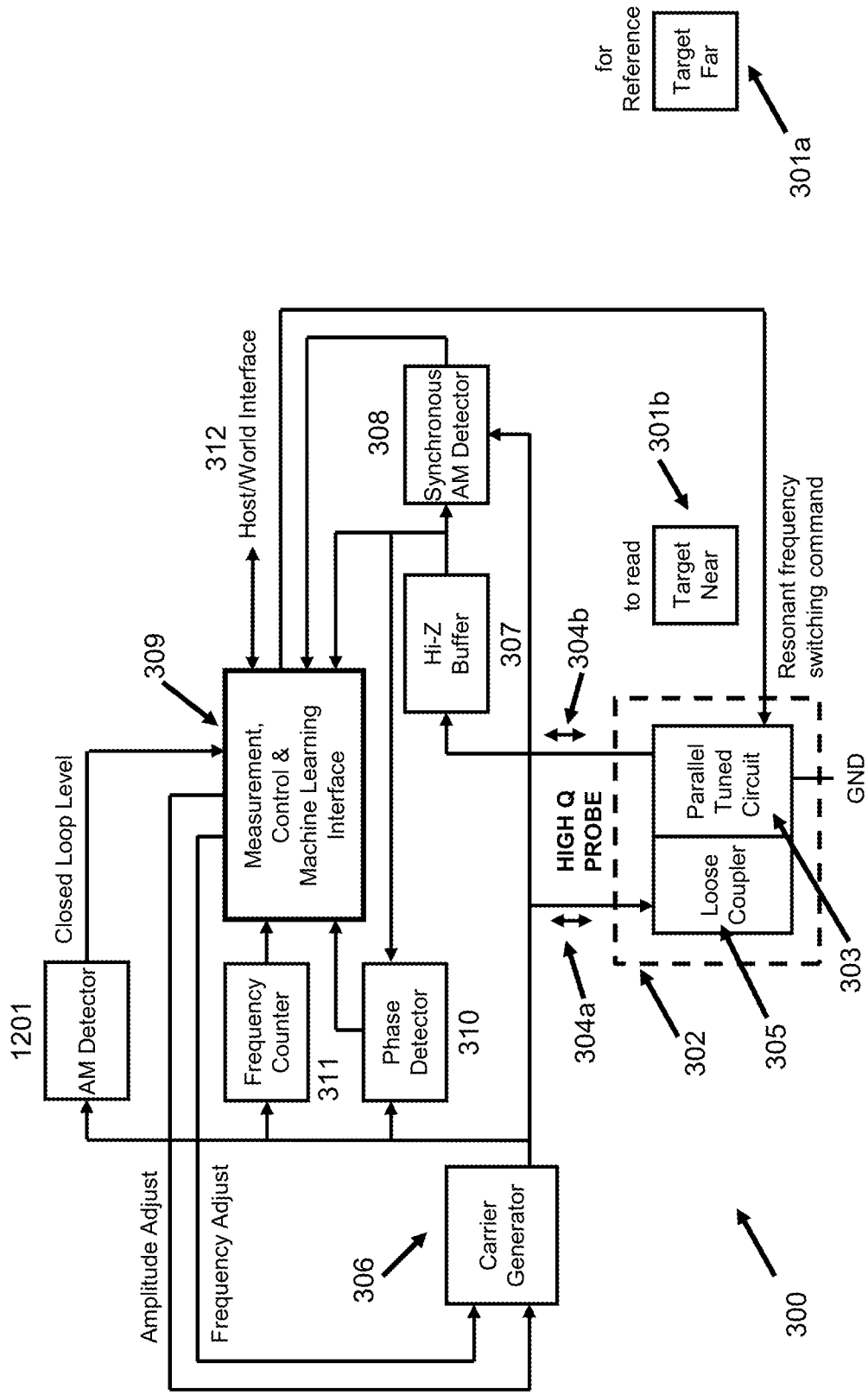
FIG. 12 is similar to FIG. 7, but with an additional AM Detector block that facilitates teaching multiple methods to obtain loss measurements of the target.

FIG. 12 shows another copy of FIG. 3 in Patent application U.S. application Ser. No. 15/082,638, filed 28 Mar. 2016. In this case, AM Detector Block 1201 is shown explicitly. As described in detail in that application, the eddy current loss in Target 301b can be measured either by maintaining a constant input level 304a to the probe tuned circuit 303 and monitoring, at resonance, its output level 304b, or by holding said tuned circuit's output level 304b constant via a control system and monitoring its input level 304a. AM Detector 1201 reads the input level at all times.

The latter configuration may be preferable; as magnetic flux density within the target is maintained at a constant value, regardless of losses therein. By setting the demanded level at 304b, and thus field strength within the target, to different values for different operating modes, it may be possible to vary the target penetration amount. As explained later in the instant disclosure, varying target penetration depth could assist with removal of unwanted artifacts.

Figure 13:
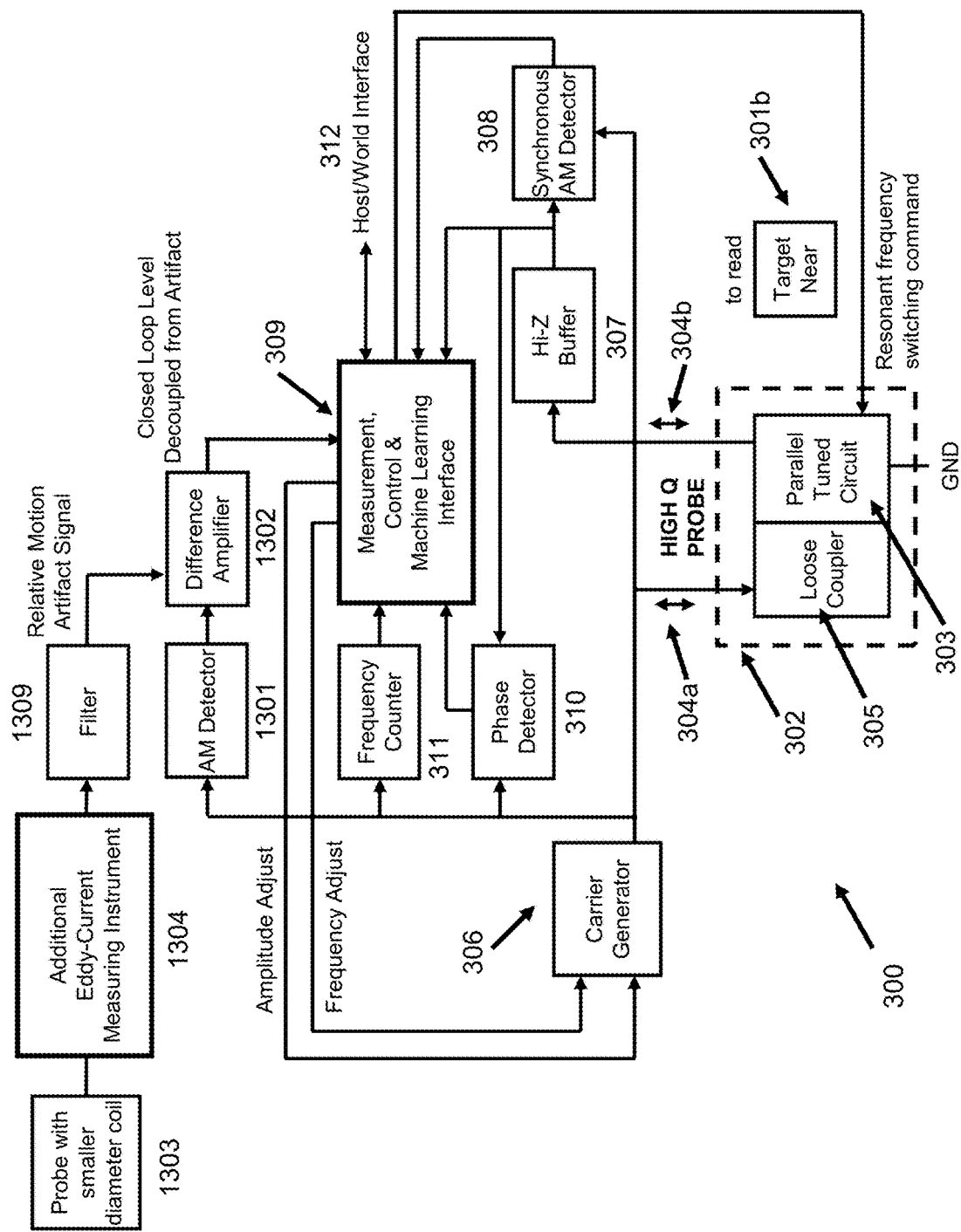
FIG. 13 shows a more detailed block diagram, as an example to implement the idea in FIG. 6—how motion artifact signal cancellation could be applied to an actual instrument, using an additional eddy current instrument with a smaller probe.

FIG. 13 shows a more detailed block diagram, as an example to implement the idea in FIG. 6—how motion artifact signal cancellation could be applied to an actual instrument. The 300-series blocks comprising an example of a complete eddy current instrument, have been again copied from FIG. 3 of U.S. application Ser. No. 15/082,638, filed 28 Mar. 2016.

High Q eddy current probe 302 corresponds with Internal Organ Target 611 in FIG. 6. "Probe with smaller diameter coil" 1303 corresponds with Dermis Target 612 in FIG. 6. As explained with FIG. 6, Coil 1303 is small enough that magnetic induction fields from it penetrate only to the Subject's skin tissue. Therefore, Additional Eddy Current Measurement Instrument 1304 cannot deliver loss information from internal organs; so the only loss signal information from Filter 1309 is related to the distance between the equipment platform comprising both eddy current instruments and the Subject's body, the motion artifact signal.

In contrast, AM Detector 1301 is an output of the main eddy current instrument 300, that uses High Q Probe 302, whose parallel tuned circuit 303 includes a coil that is large enough to produce a magnetic induction field that permeates internal organs as well as outer skin layers. Therefore, AM detector 1301 delivers both the desired internal organ loss signal and the undesired motion artifact signal. When these two signals are delivered to Difference Amplifier 1302 with the correct relative amplitudes, the motion artifact signal will be cancelled at its output.

The sensor, in this case Blocks 1303 and 1304, that is applied to detect the offending artifact in favor of the desired signal may itself be subject to unwanted noise or physical variables that differ from those detected by the main sensor, Probe 302. If the unwanted noise or physical variable signals are primarily absent from the portion of the spectrum occupied by the artifact, Filter 1309 or a set of filters can be used to reduce them.

It should be understood that many eddy current instrument designs can be used for Blocks 1303 and 1304; there may be no need to match the design of Block 300. Moreover, Blocks 1303 and 1304 need not be an eddy current instrument but could be any type of instrument that is not sensitive to the desired data of Block 300 but is sensitive to some particular artifact that adversely affects said data. Likewise, Block 300 can represent any eddy current instrument design.

Figure 14:
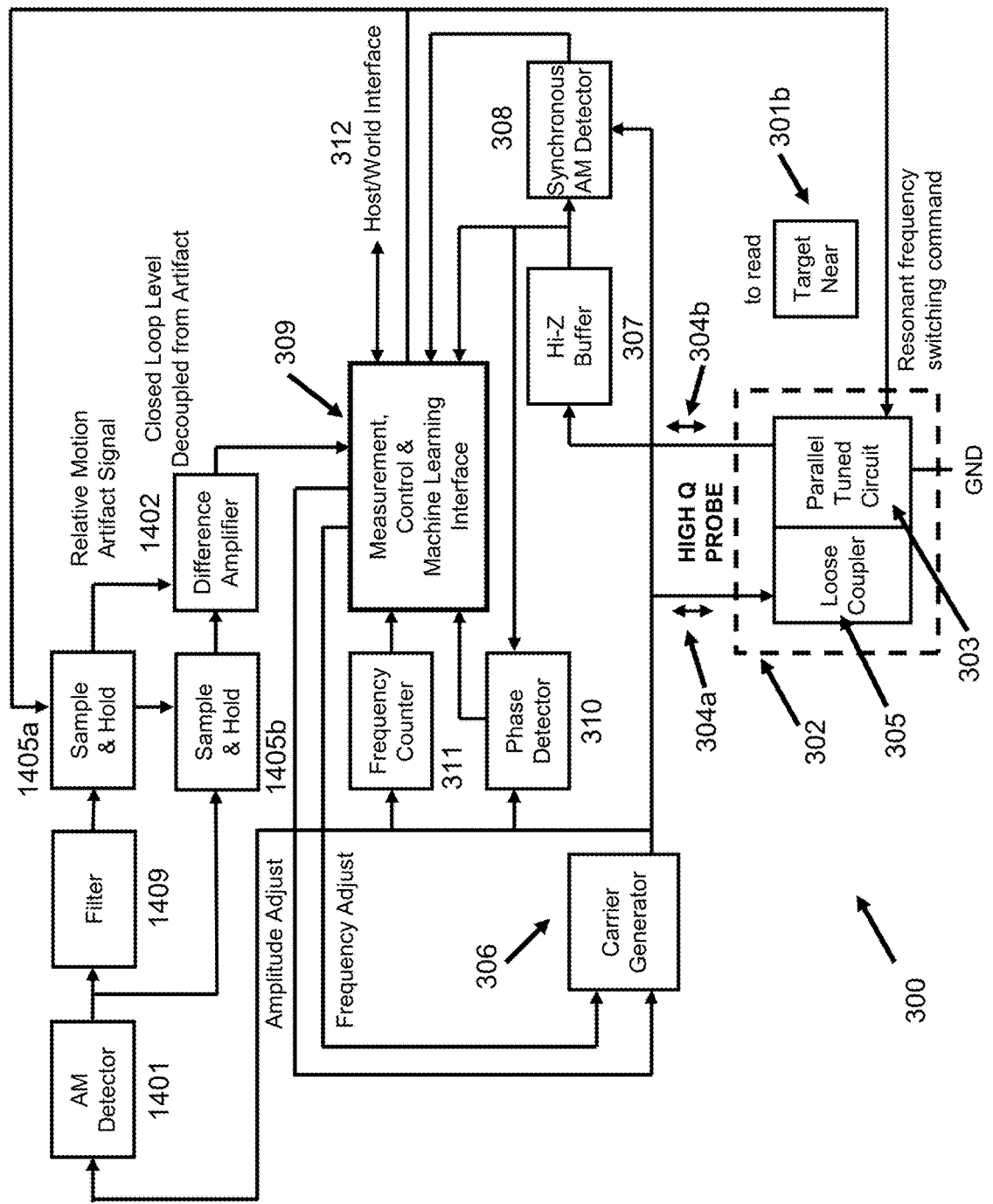
FIG. 14 shows a second more detailed block diagram, as an example to implement the idea in FIG. 6—how motion artifact signal cancellation could be applied to an actual instrument, but requiring sample and hold circuitry instead of an auxiliary eddy current instrument or probe.

FIG. 14 shows another copy of FIG. 3 in Patent application U.S. application Ser. No. 15/082,638, filed 28 Mar. 2016. For this embodiment, the auxiliary magnetic probe is not needed, and neither is the auxiliary eddy current measurement circuitry.

Referring again to FIG. 6, the objective is to eliminate or suppress the motion artifact in favor of the information about internal organs, tissues, and fluids, by subtracting a signal representing only the distance between the instrument and the body from the main signal, that represents a composite of this distance and internal bodily information. Any signal that captures only the motion could be used for this purpose. In FIG. 13, the signal comes from an auxiliary eddy current measurement instrument connected to probe tuned circuit coil that is small enough to prevent a significant magnetic field from penetrating the body but large enough to reach its outer layers.

FIG. 14 shows an embodiment that accomplishes the same goal by either lowering the magnetic field flux density, lowering the field frequency, or both. As described in detail in the text for FIG. 3 of said previous patent application, the embodiment is capable of regulating frequency of carrier generator 306, the magnetic probe parallel tuned circuit resonant frequency, output amplitude of the carrier generator, and demanded output level of said tuned circuit. As further explained, the tuned circuit output level is directly related to its circulating current and thus, the flux density level wherever the flux exists.

As further described, when operating in closed loop mode, the carrier generator output voltage level represents the eddy current loss for whatever medium is permeated by the magnetic field from the probe. If the field level is controlled to be high enough, eddy current loss of the body surface tissue and internal tissue is measured; if the field level is controlled to be sufficiently reduced, eddy current loss of only the body surface tissue is measured. If the field level is not reduced, but the field frequency is reduced, a similar effect occurs.

The embodiment shown in FIG. 14 differs from that of FIG. 13 in that it includes a means to eliminate the auxiliary eddy current measurement circuitry. Under direction of Controller 309, the instrument switches back and forth between the high field level and/or high frequency output state to a low field level and/or low frequency state. The switching frequency is high enough that changes of relative position and internal bodily function are sufficiently small for any one switching cycle. Therefore, Sample & Hold blocks 1405$a,b$ allow Difference Amplifier 1402 to remove relative position data as if there were two eddy current instruments. When parallel tuned circuit output 304$b$ level and parallel tuned circuit 303 resonant frequency are both high enough for the magnetic fields to reach both the outer tissues and internal tissues, organs, and fluids of the body, Sample and Hold 1405$b$ is controlled to the Sample state, and the Sample and Hold 1405$a$ is controlled to the Hold state. When either the parallel tuned circuit output 304$b$ level or parallel tuned circuit 303 resonant frequency are high enough for the magnetic fields to reach the outer tissues but not internal tissues, organs, and fluids of the body, Sample and Hold 1405$a$ is controlled to the Sample state, and the Sample and Hold 1405$b$ is controlled to the Hold state. Filter 1409 thus acts only on the artifact-only condition, similar to Filter 1309 in FIG. 13, and has the same purpose.

Figure 15:
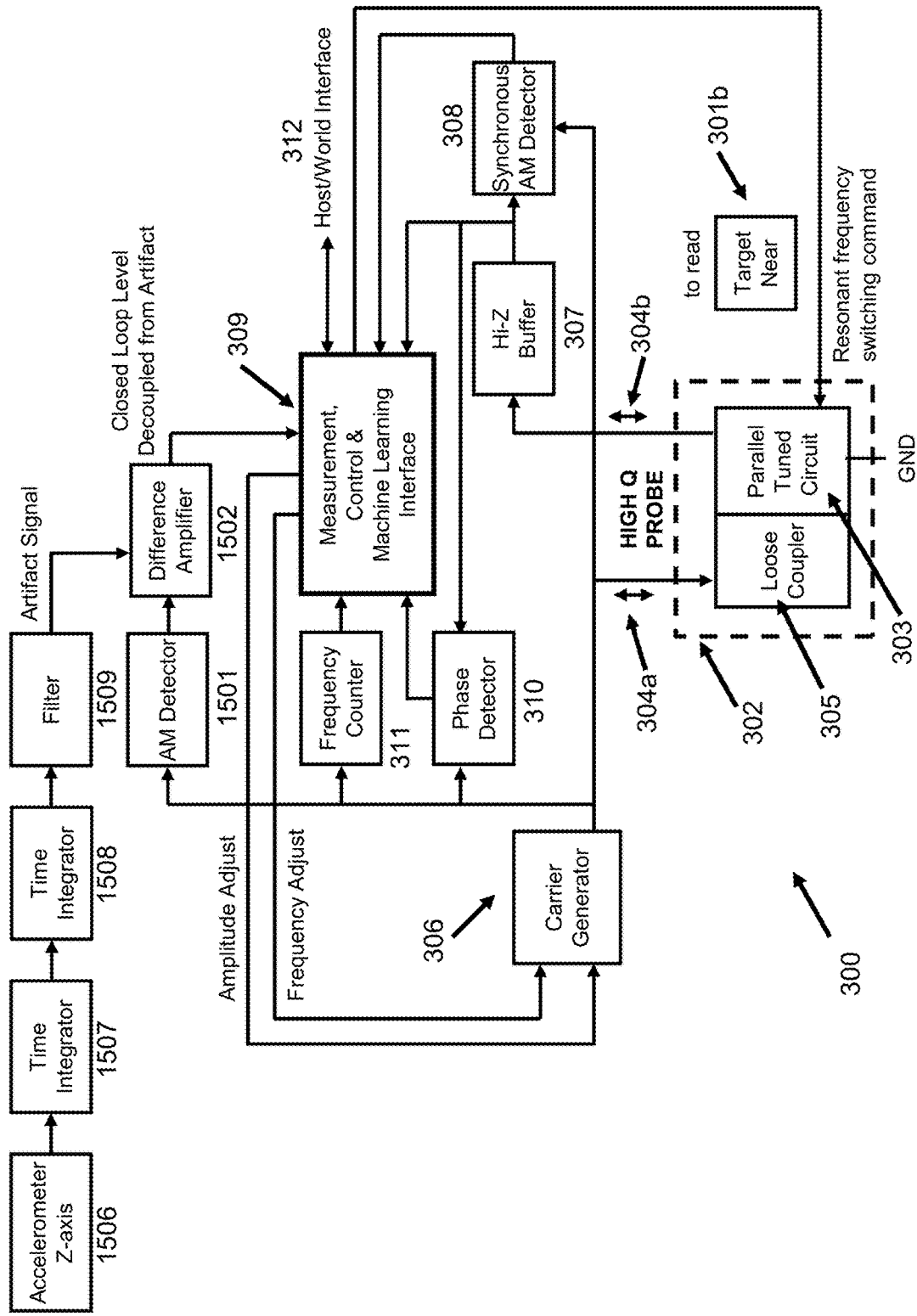
FIG. 15 shows a third more detailed block diagram, as an example to implement the idea in FIG. 6—how motion artifact signal cancellation could be applied to an actual instrument, but requiring an accelerometer and time integrator circuitry instead of an auxiliary eddy current instrument or probe.

FIG. 15 shows yet another copy of FIG. 3 in Patent application U.S. application Ser. No. 15/082,638, filed 28 Mar. 2016. Added to this figure are functional blocks pertaining to another example method to cancel the motion artifact. This embodiment requires neither an auxiliary eddy current instrument nor a sample and hold block to subtract the motion artifact signal from the composite signal. Inasmuch as the body mounted sensor/instrumentation/communication system could include a vector accelerometer, the z-axis sensor 1506 is connected to a double integrator 1507, 1508. Filter 1509 has the same purpose as Filters 1409 and 1309 in FIGS. 14 and 13.

Not shown in FIG. 15 are Integrators 1508 and 1507 being reset by Control block 309 to zero whenever the clothing, attached to the instrument assembly, is in a fiduciary position and stationary, such as touching the skin. This position can be detected by averaging the maximum eddy current losses.

Figure 16:
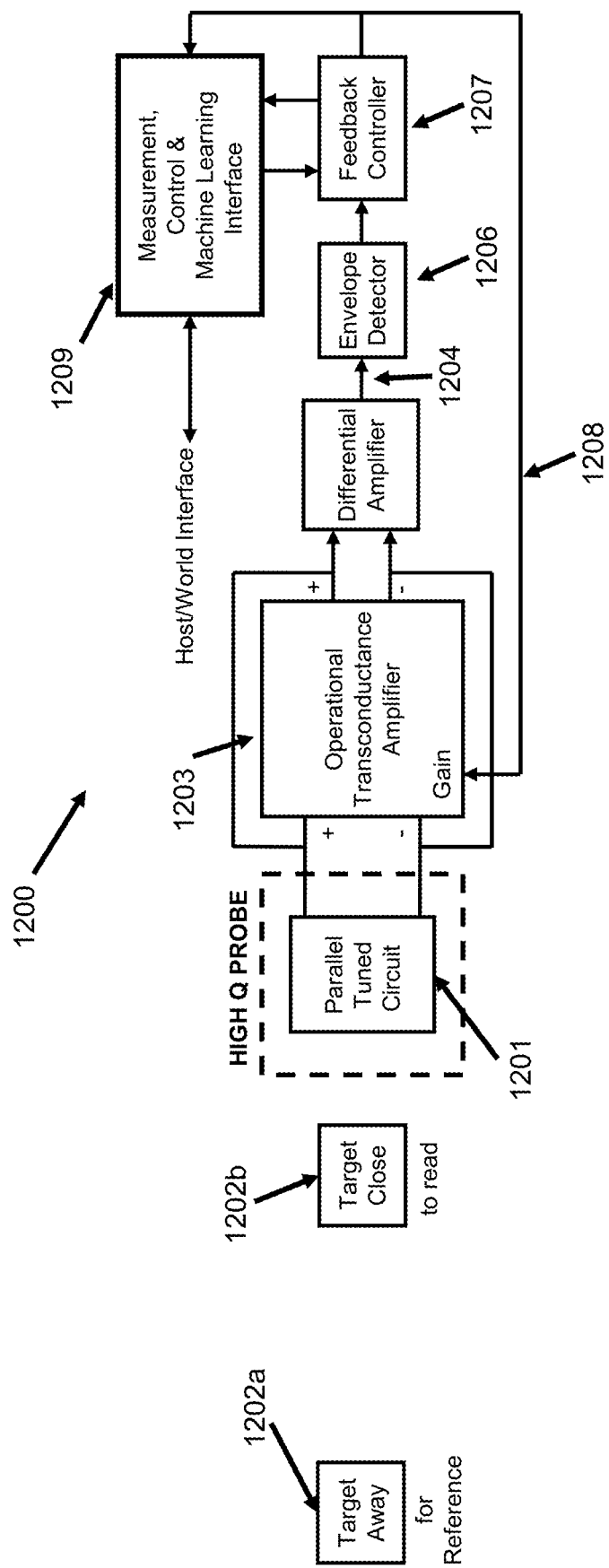
FIG. 16 shows a block diagram of an eddy current instrument wherein the parallel tuned circuit that includes the probe coil is also the oscillator tank circuit.

FIG. 16 shows a copy of FIG. 12 in Patent application U.S. application Ser. No. 15/082,638, filed 28 Mar. 2016. As explained in much detail in paragraphs 0092 to 0098 of that filing, for this embodiment in that disclosure, the parallel tuned circuit in the eddy current probe is the oscillator tank circuit, instead of being driven passively by a carrier source that is regulated in frequency to match tuned circuit resonance. It is an example of a negative resistance means to maintain a constant output from an oscillator as the effective parallel tuned circuit parallel resistance is varied by eddy current losses within a target. United States patent application #20030071638, 17 Apr. 2003, Inventor Olaf Machul, originally filed in Germany as Application #10143900.8, 7 Sep. 2001, may be one of the first to publicize this idea.

Figure 17:
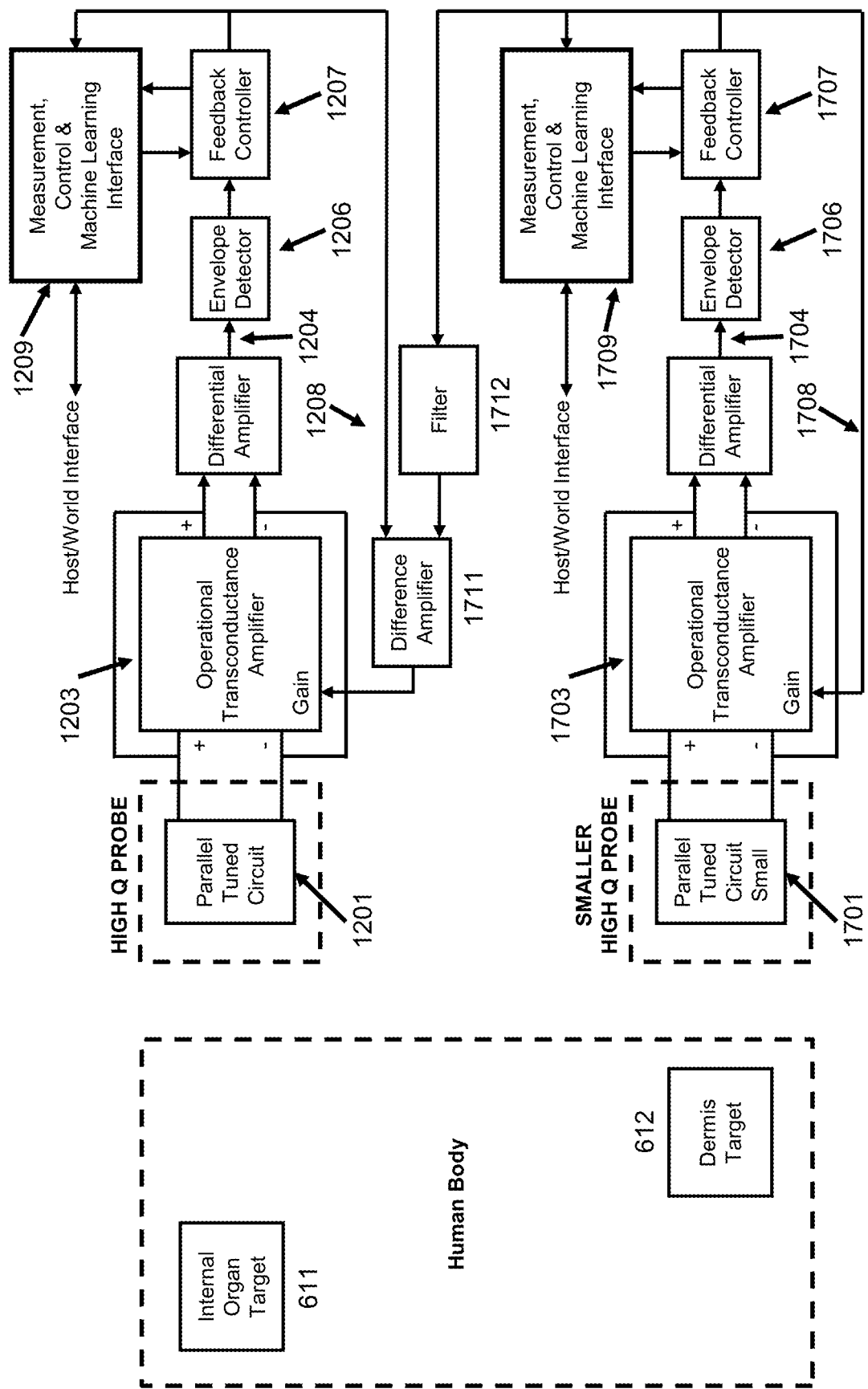
FIG. 17 shows two eddy current instruments as shown in FIG. 16 that operate together per FIG. 6 and FIG. 13.

FIG. 17 starts with a copy of FIG. 12 in U.S. application Ser. No. 15/082,638, filed 28 Mar. 2016. The intention is to illustrate the idea in FIG. 6, that a variety of eddy current measurement instrument types can be used to remove a motion artifact from the data. There are two instruments on the same equipment platform. The instrument with 1700-series numbering uses a probe with a smaller parallel tuned circuit coil; so it's magnetic induction fields can penetrate only as far Dermis Target 612, whereas the coil in Parallel Tuned Circuit 1201 is large enough that its fields penetrate all the way to internal organ target 611. Filter 1712 and Difference Amplifier 1711 have the same functions as Blocks 1309 and 1302 in FIG. 13.

Figure 18:
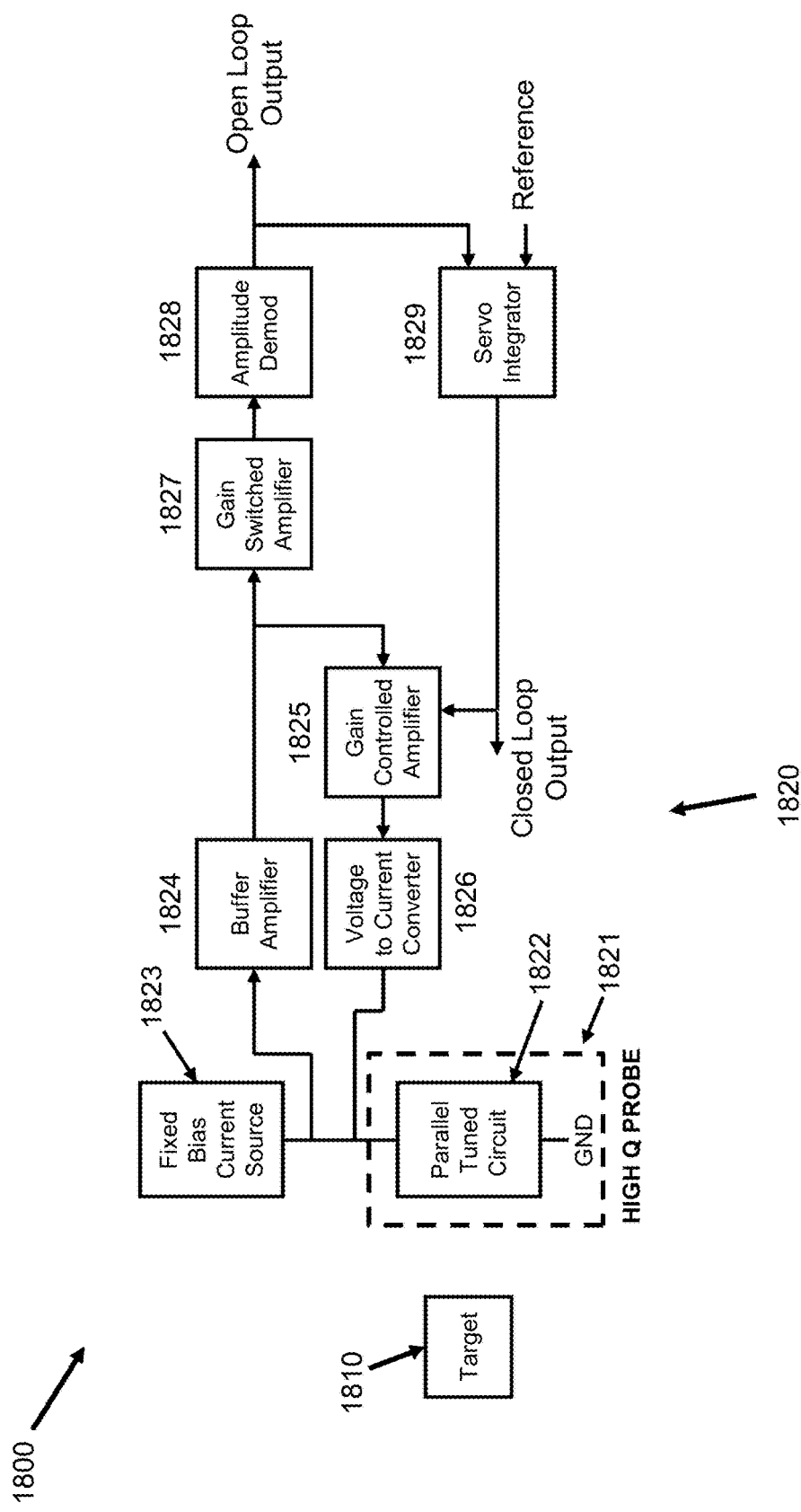
FIG. 18 shows another basic eddy current measuring instrument for which the sensing probe parallel tuned circuit is the tank component of an oscillator. Its main feature is a combination of outputs—a closed loop wide dynamic range, and open loop for expanded detail of any narrow range.

FIG. 18 shows another basic eddy current measuring instrument 1820, for which the sensing probe 1821 parallel tuned circuit 1822 is the tank component of an oscillator. Operation of this basic type instrument is described in detail in U.S. application Ser. No. 15/082,638, filed 28 Mar. 2016, and in some number of issued patents, such as U.S. Pat. No. 8,432,169, inventors Niwa et. al. and assigned to Panasonic Corp.

The resonant frequency of tuned circuit 1822 determines the frequency of oscillation. The oscillator feedback path consists of buffer amplifier 1824, gain controlled amplifier 1825, and voltage to current converter 1826. Its basic function is to supply sufficient power at the resonant frequency and correct phase to replace the power lost in tuned circuit 1822. Fixed Bias current source 1823 determines the oscillator amplitude operating point.

Gain switched amplifier 1827, amplitude demodulator 1828, and servo integrator 1829 comprise a measurement and control system to maintain the oscillator output power level from buffer amplifier 1824 constant. Servo integrator 1829 varies the gain of gain controlled amplifier 1825 until the demodulated voltage at amplitude demodulator 1828, representing the oscillator power level, is equal to the dc voltage at its Reference input. Typically, this Reference voltage is fixed to match the center of Amplitude Demodulator 1828 linear range. Gain switched amplifier 1827 is set to cause the desired amplitude from buffer amplifier 1824 to be transformed to the amplitude needed to operate amplitude demodulator 1828 at the center of its linear range, under the same conditions that buffer amplifier 1824 is delivering a voltage level representing the smallest amount possible to reliably sustain oscillator operation.

In order to sustain oscillation, said feedback path (loop) must inject a minimum amount of power to cover losses of the tuned circuit. If said measurement and control system is adjusted to demand at all times the minimum buffer amplifier 1824 output voltage for which oscillation is sustained, servo integrator 1829 output level can be considered as a scale to represent losses of tuned circuit 1822. As previously described, losses seen at the tuned circuit result from losses therein plus those within the eddy current target 1810. "Closed Loop Output" delivers a very wide range of loss values of Target 1810. Inasmuch as parallel tuned circuit 1822 has a very high Q, almost all of the losses measured are within target 1810.

In closed loop operation shown in FIG. 18, "Open Loop Output" voltage remains constant. If eddy current measurement details within a narrow range are desired, servo integrator output voltage could be frozen after the desired loss range has been identified. This would cause said feedback path to have a constant gain, thus enabling target 1810 loss changes to be registered at the "Open Loop Output".

Under the conditions stated above, that the gain controlled set point operates the oscillator at just high enough amplitude to maintain operation, when the control loop is frozen, there could be a considerable open loop range as the eddy current loss decreases, but very little range as the eddy current loss increases. Therefore, when a combination of closed and open control loop operation is desired, it may be desirable to operate buffer amplifier 1824 at somewhat lower gain; so that under closed control loop operation, the oscillator is not running at the minimum level needed to sustain oscillation.

Figure 19:
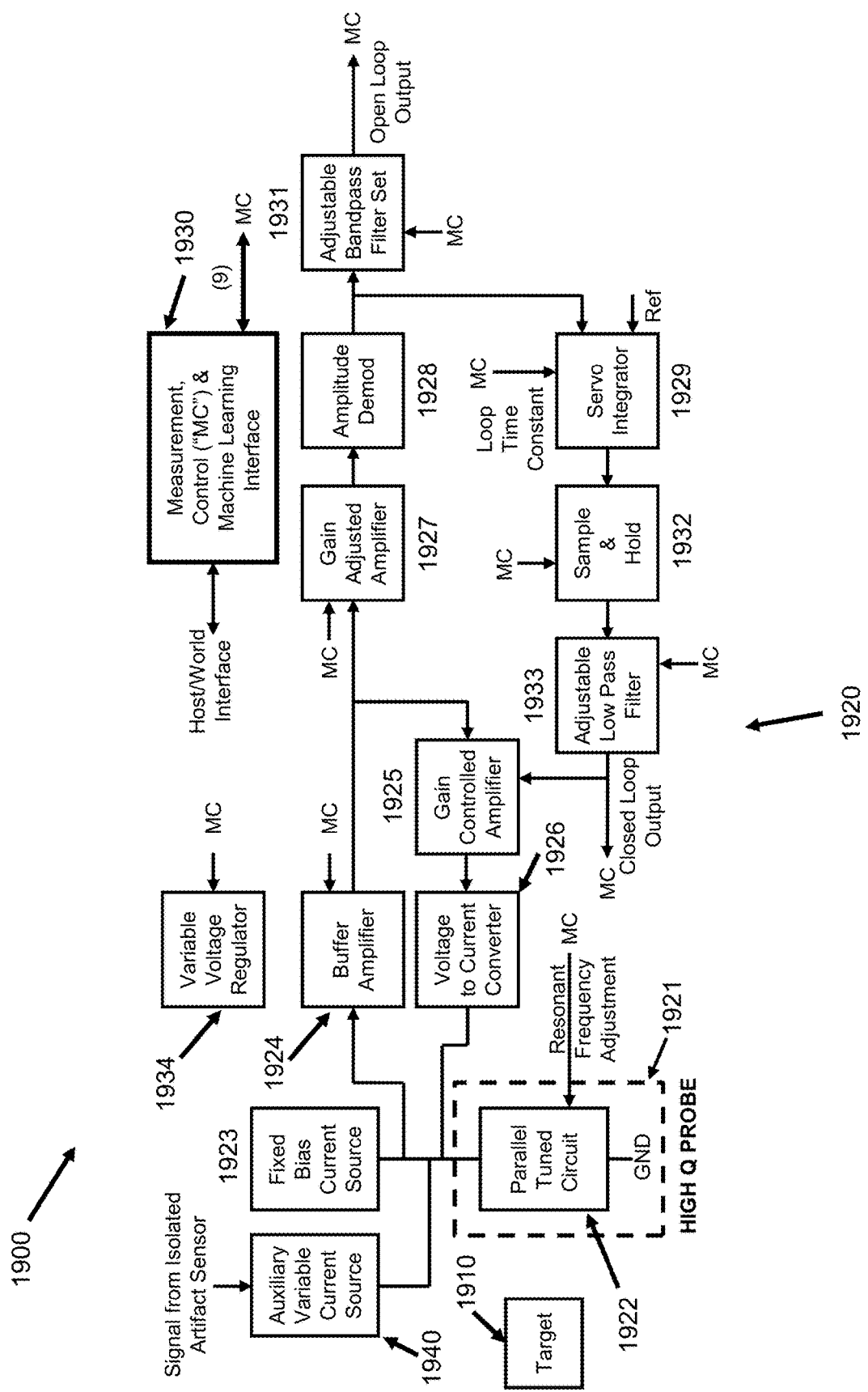
FIG. 19 shows an embodiment that embellishes the design shown in FIG. 18. In addition to expanding quickly to focus on a narrow range of eddy current loss, the removal of various unwanted artifacts is supported.

FIG. 19 is similar to FIG. 18. Certain embellishments were added (1930-series designations) to show implementation to focus on narrow range eddy current measurements after this range has been identified quickly. Other embellishments were added to facilitate the removal of unwanted artifacts. Measurement, Control & Machine Learning Interface 1930 directs the operation of every block shown connecting to "MC".

In closed loop operation, the measurement scale includes a very wide range of eddy current loss values, but often, the desired data consists of minute variations around an average value. Therefore, once the steady state value exists at the Closed Loop Output, Sample and Hold 1932 can be switched from Sample to Hold mode, freezing the gain of amplifier 1925. In this mode the instrument is operating with an open control loop, and the Open Loop Output signal is centered on the steady state value and will deliver voltage changes reflecting small eddy current loss variations.

In another mode of operation, once the steady state value exists at the Closed Loop Output, Sample and Hold 1932 could remain in the Sample condition instead of switching to Hold, while Servo Integrator 1929 time constant can be switched from short to long. This operating mode is useful when the minute desired signal has short-term features. As a specific example, Probe 1921 could at first be separated from a human body, resulting in almost no eddy current loss. When Probe 1921 is placed close enough to the body there is a drastic eddy current loss increase from internal tissues, which would register at the Closed Loop Output. Riding on this new and larger eddy current loss are minute loss changes resulting from blood rushing into and out of the heart, with, say a 1-second period. With Servo Integrator switched to a relatively long time constant, such AC variations would be too rapid for the control system to follow; so only the Open Loop output will contain this signal, to measure heart rate and other cardiac functions.

For both Sample and Hold and variable servo integrator time constant modes explained in the previous two paragraphs, the Open Loop Output scales could be non-linear or truncated in the direction of increased eddy current losses when closed control loop operation demands oscillator output level at buffer amplifier 1924 to be only high enough to sustain oscillator operation. By decreasing buffer amplifier gain to increase the demanded oscillator output level to be somewhat above that value needed to sustain oscillation, the Open Loop Output scale could be extended and/or more symmetrical in the lower and higher eddy current loss direction.

Filter 1931, which could include a tracking filter, could be relatively narrow band centered on the instantaneous heart rate frequency or other artifact signal frequency in order to increase signal to noise ratio. Not specifically shown could be a tandem set of filters: a phase locked loop tracking filter could provide repetition rate/frequency information that could be used to set the peaking frequency of a switched capacitor or other analog filter to capture and track waveform and amplitude of the cardiac based effect.

As covered earlier in the instant disclosure, there may be a need to make use of two (or more) eddy current loss signals, one that is sensitive to internal organs and one that is sensitive only to outer tissues, such as to measure relative motion of the instrument and body. Two of the several methods described in the instant disclosure to regulate penetration of magnetic fields into a body or other target are represented separately in FIG. 19. Both of these methods are shown as controlled by Controller 1930, which can therefore determine the amount of penetration at specific times and compare signal characteristic to remove motion and other artifacts.

Variable voltage regulator 1934 controls the power supply voltage to amplifier 1924 and trans-conductance amplifier set 1925/1926. The supply voltage on these blocks determines the AC current values circulating within tuned circuit 1922, which in turn determines magnetic flux density within the target. Controller 1930 also can adjust the resonant frequency of tuned circuit 1922, determining the oscillating frequency and that of the magnetic flux permeating target 1910. The higher the frequency, the more the penetration.

Auxiliary Variable Current Source 1940 functions similarly to fixed bias current source 1923 and Voltage to Current Converter 1926. Instead of providing a fixed amount of current as 1923, it provides a current value based upon an input baseband voltage representing an unwanted artifact signal from a sensor that responds only to that artifact. For example, this could be from relative motion of the target/subject and the instrument. For example, the artifact sensor could be an additional eddy current loss instrument or some other motion or relative motion detector. Such an artifact signal is additive to the Closed or Open Loop Output.

Figure 20:
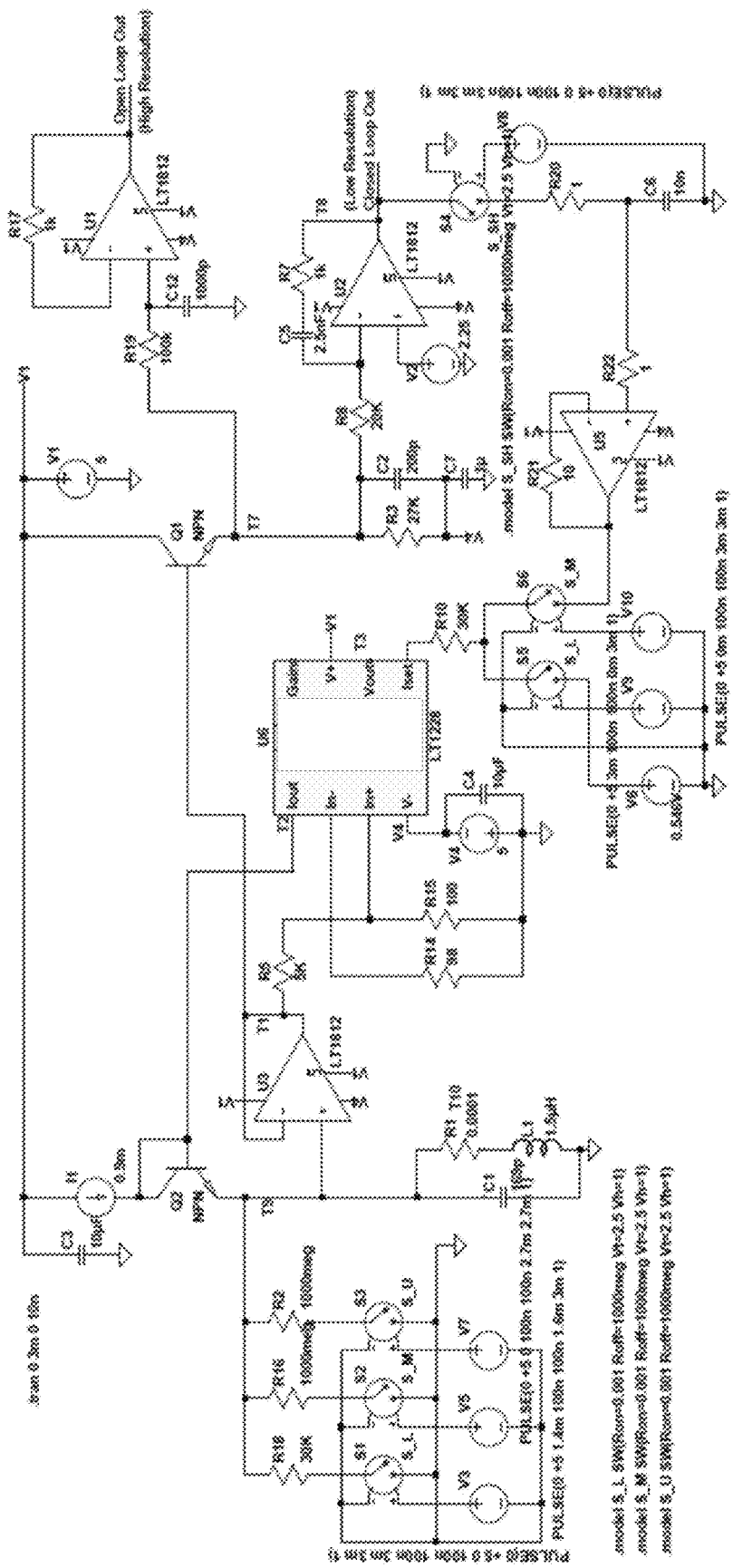
FIG. 20 shows a simulated schematic of the block diagram of FIG. 18.

FIG. 20 shows a simulated schematic of the block diagram in FIG. 18. L1/C1/R1 details the parallel tuned circuit 1822. R18 is the tuned circuit shunting resistance Rp representing the eddy current loss from target 1810. U3 details buffer amplifier 1824. U6, a trans-conductance amplifier integrated circuit details gain controlled amplifier 1825 and voltage to current converter 1826. I1 and Q2 represent fixed bias current source 1823. Q1, R3, and C2 comprise amplitude demodulator 1828. U2, C5, R8, and R7 comprise servo integrator 1829.

Increased eddy current loss is accurately modeled by the decreased value of R18, ("Rp"). The control loop integrator U2 creates a higher voltage for R10, in turn resulting in a higher current into U6, "Iset", thus causing U6 to have a higher transconductance to maintain a constant level T1 at U3, the oscillator output. The objective of the simulation schematic in FIG. 20 is to test the idea of auxiliary variable current source 1940 in FIG. 19 by varying the fixed bias current 1823/1923/I1 for many values of R18. The simulation results show that an external signal can be used to effect the eddy current loss instrument output.

Figure 21:
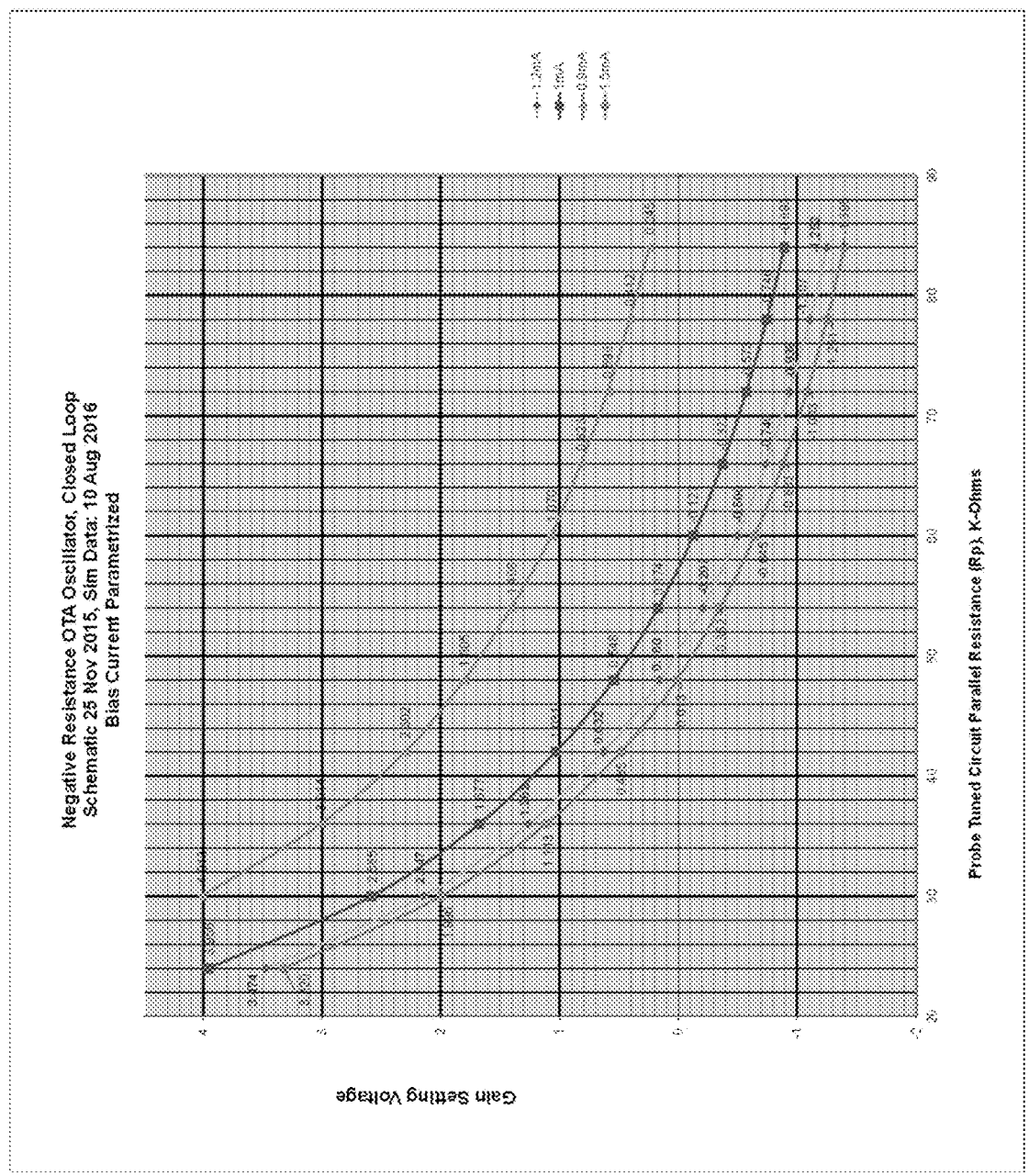
FIG. 21 shows a family of transfer characteristic curves of the eddy current loss instrument shown in FIG. 20.

FIG. 21 shows a family of transfer characteristic curves of the eddy current loss instrument shown in FIG. 20, where the abscissa is the Rp value representing eddy current loss and the ordinate is the closed loop gain setting voltage, termed "Closed Loop Output" in FIGS. 18 and 19. The curves are well behaved and cover the wide range between 24K and 84K. The parameter is fixed bias current.

Figure 22:
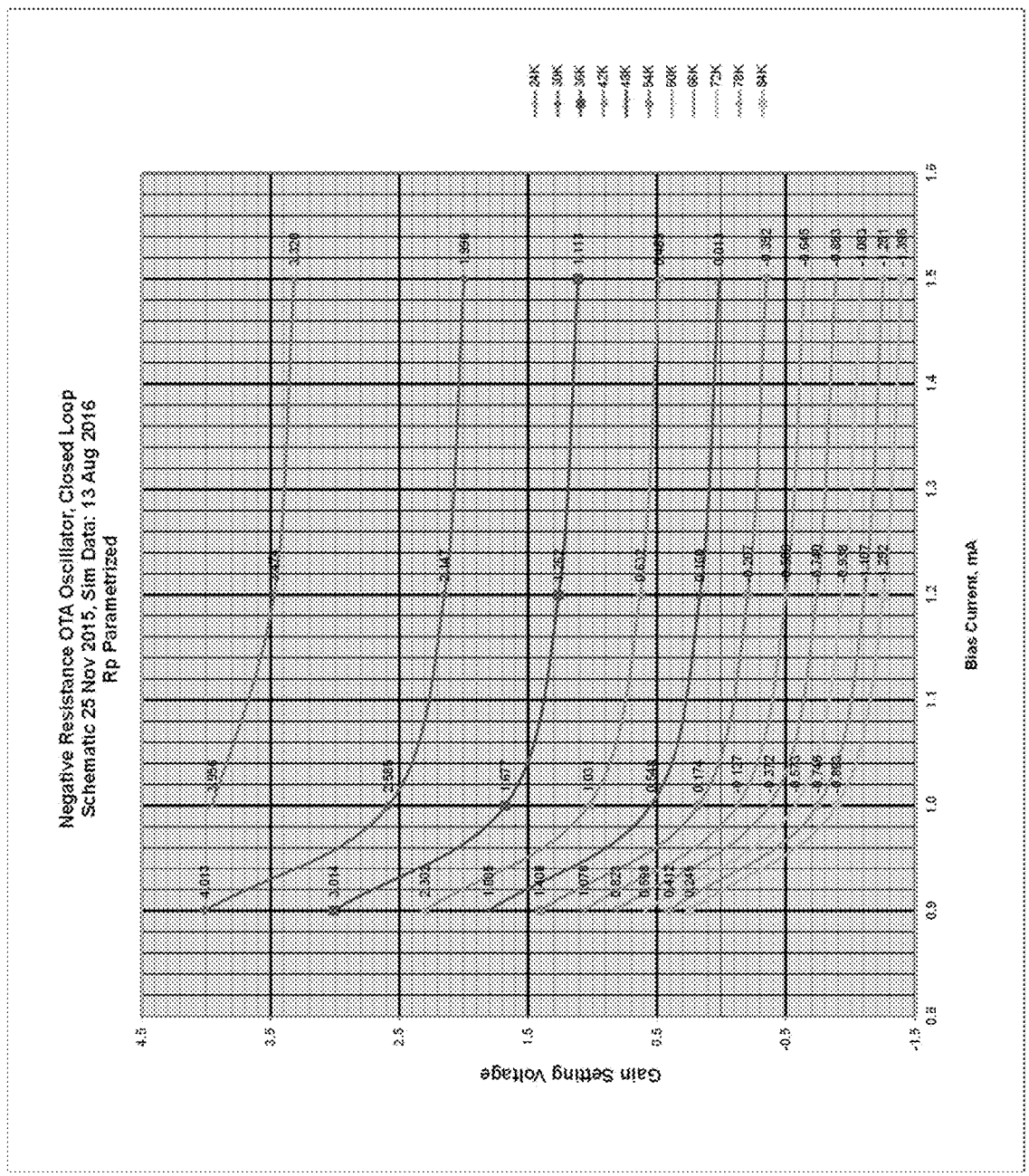
FIG. 22 uses the same simulated data as FIG. 21, but here, for each parametrized eddy current loss value, the effect on Closed Loop Output by bias current is studied.

FIG. 22 uses the same simulated data as FIG. 21, but here, for each parametrized Rp loss value, the effect on Closed Loop Output by bias current is studied. As seen, the transfer curves for external sensor signals are also well behaved, with linear and curved portions. They could be used to select the transfer gain. Lack of linearity is not a problem for small signal cases. Setting the oscillator output to be controlled to a higher level than that needed to sustain oscillation may increase the linear range of these transfer curves.

The details provided in the above description, including the figures describe particular implementations of the systems for performing the measurements described. Other embodiments could be implemented in any other suitable manner. For example, particular voltages, frequencies, noise levels, gains, resistances, capacitances, and other values are described. These values are for illustration only. It may be advantageous to set forth definitions of certain words and phrases used throughout this patent document. The term "couple" and its derivatives refer to any direct or indirect communication between two or more elements, whether or not those elements are in physical contact with one another. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. An electromagnetic imaging instrument to measure internal properties and movement of a target object within a container or body, where there is also a spurious relative motion of the instrument and the container or body, the instrument comprising:
   an eddy current measuring apparatus that outputs a composite signal containing information about said internal properties and movement of the target object contaminated with information about the spurious relative motion;
   an auxiliary motion sensing means driving an auxiliary motion sensing means processing circuitry having an auxiliary motion sensing means processing circuitry output signal that contains only information about the spurious relative motion; and
   a difference measuring circuit to output a signal that subtracts a value of one signal from another, wherein, the composite signal is fed to a first input of the difference measuring circuit and the auxiliary motion sensing means processing circuitry output signal is fed to a second input of the difference measuring circuit, and
   a signal processing means, wherein the signal processing means output contains less contamination from information about the spurious relative motion than the composite signal.

2. The system of claim 1, wherein: the auxiliary motion sensing means processing circuitry includes filtering to obtain spectral components of the spurious relative motion.

3. The system of claim 1: where the relative motion of the instrument and the container or body signal is caused by accelerating motion of the instrument, the auxiliary motion sensing means processing circuitry comprising:
   an accelerometer, measuring an instantaneous acceleration of the instrument, driving a 1st time integrator circuit to provide a velocity signal from the accelerometer, driving a 2nd time integrator circuit to provide a position signal from the 1st time integrator circuit, a means to initialize said integrator circuits whenever the instrument is touching the surface of the container or body, and additional accelerometer and integrator processing circuitry, where the 2nd time integrator circuit and the composite signal each feed an input of a difference amplifier input whereby the difference amplifier output contains less contamination from information about the spurious relative motion than the composite signal.

4. The system of claim 1: where the eddy current measuring apparatus is comprised of a frequency agile monochromatic carrier generator coupled to a passive parallel tuned circuit probe containing a coil inductor and capacitors, wherein the probe has a quality factor (Q) value range from 50 to 500,
   means to measure and adjust the generator frequency, wherein the frequency range comprises a resonant frequency of the parallel tuned circuit and offsets to the resonant frequency, wherein the offsets comprise a range designed to measure loaded Q values of the probe, an AM detector configured to measure and adjust the generator output level, means to measure a phase difference between an input and output of the parallel tuned circuit, means to measure the output level of the parallel resonant circuit, and a feedback loop circuitry, comprising a phase detector and a loop filter, to maintain the output level of the parallel tuned circuit constant, regardless of the target object's eddy current loss, wherein the eddy current sensing apparatus output signal comes from the parallel tuned circuit input, as a measurement of the target object's eddy current loss.

5. The system of claim 4, wherein: the feedback loop circuitry output level and the input level of the parallel tuned circuit are frozen at a point within the measurement range of the eddy current measurement apparatus, whereby the output level of the parallel tuned circuit will vary in accordance with incremental eddy current losses of the target object.

6. The system of claim 4, wherein: the auxiliary motion sensing means is comprised of an auxiliary eddy current measurement apparatus identical to the eddy current measurement apparatus, except that a coil inductor of the auxiliary eddy current measurement apparatus' parallel tuned circuit is sufficiently small that eddy currents are induced only at the proximal surface of the container or body, whereby an output signal contains information only about spurious relative motion of the instrument and the container or body.

7. The system of claim 4: wherein:
the auxiliary motion sensing means processing circuitry includes a means to switch the resonant frequency of the eddy current measurement apparatus back and forth between a higher frequency and a lower frequency, where operation of the eddy current measurement apparatus at the higher frequency permits eddy current penetration to the target object enabling the eddy current measurement apparatus to deliver the composite signal, and
operation at the lower frequency permits eddy currents only at the proximal surface of the container or body, whereby the eddy current measurement apparatus output signal contains information only about the spurious relative motion of the instrument and the container or body, where a sample and hold circuit causes the reading from the eddy current measurement apparatus at one frequency to exist while said apparatus is operating at the other frequency; and
subtraction of the spurious relative motion signal from the composite signal occurs in the different measuring circuit.

8. The system of claim 4, wherein: the auxiliary motion sensing means processing circuitry includes a means to switch the parallel resonant circuit of the eddy current measurement apparatus back and forth between a higher power level and a lower power level, where operation of the parallel resonant circuit at the higher power permits eddy current penetration to the target object enabling the eddy current measurement apparatus to deliver the composite signal, and operation parallel resonant circuit at the lower power level permits eddy currents only at the proximal surface of the container or body, so that the eddy current measurement apparatus output signal contains information only about the spurious relative motion of the instrument and the container or body;
a sample and hold circuit causes the reading from the eddy current measurement apparatus at one parallel resonant circuit power level to exist while said apparatus is operating at the other power level; and
subtraction of the spurious relative motion signal from the composite signal occurs in the difference measuring circuit.

9. An electromagnetic imaging eddy current instrument to measure internal properties and movement of a target object within a container or body, where there is also a spurious relative motion of the instrument and the container or body, the instrument comprising:
an oscillator whose tank circuit consists of a parallel tuned circuit that includes a coil inductor also functioning as an eddy current probe, where the parallel tuned circuit is connected to an input of a buffer amplifier, an output of a voltage-to-current converter, a fixed bias current source and an auxiliary variable bias current source driven by a sensor means that measures the spurious relative motion of the instrument and the container or body;
where the buffer amplifier feeds a signal input of a gain-controlled amplifier, which in turn feeds an input of the voltage-to-current converter;
where the parallel tuned circuit, the buffer amplifier, the gain-controlled amplifier, and the voltage-to-current converter constitute the oscillator, where the buffer amplifier also feeds an amplitude demodulator which in turn feeds a signal input of a servo integrator;
where the servo amplifier, through a cascaded sample and hold circuit in the sample mode and a low pass filter complete a closed control loop by feeding a control input of the gain-controlled amplifier;
whereby the closed control loop maintains the oscillator output and the amplitude demodulator output at a constant level over a wide range of losses reflected to the parallel tuned circuit by the target object and container or body, as corrected for the spurious relative motion of the instrument and the container or body by the auxiliary variable bias current source, causing the servo integrator output level to represent only the loss reflected to the parallel tuned circuit by the target object; and
where a closed control loop mode output of the instrument is the servo integrator output.

10. The system of claim 9, where at a chosen level within the eddy current instrument measurement range, a control means connected to a control input of the sample and hold circuit switches the sample and hold circuit to the hold mode, causing the gain of the gain-controlled amplifier to be frozen to create an open loop mode;
whereby the amplitude demodulator output level varies in accordance with incremental eddy current losses of the target object, and where an open loop mode output of the instrument is the amplitude demodulator output.

11. The system of claim 10, where: during operation of the closed control loop mode, the oscillator output and the buffer amplifier signal output are maintained by a setting of a reference input of the servo integrator at a higher level than that the minimum necessary to sustain oscillation of the oscillator:
whereby when in open loop mode, the amplitude demodulator output level has an expanded and closer to linear measurement range of the eddy current loss.

12. The system of claim 9 wherein: the auxiliary variable bias current source is frozen;

the instrument measures a composite signal comprised of internal properties and movement of the target object within the container or body combined with that of the container or body, where there is also a spurious relative motion of the instrument and the container or body;

an auxiliary instrument, identical to the instrument except that the coil inductor of the auxiliary instrument's parallel tuned circuit is sufficiently small that eddy currents are induced only at the proximal surface of the container or whereby the closed loop mode and open loop mode output signals contain information only about spurious relative motion of the instrument and the container or body;

the closed loop mode outputs of the instrument and the auxiliary instrument are connected to a set of inputs of a closed loop difference amplifier, and the open loop mode outputs of the instrument and the auxiliary instrument are connected to a set of inputs of an open loop difference amplifier; whereby, the output of each said difference amplifier delivers the composite signal with the spurious relative motion signal having been removed.

13. The system of claim 9, wherein: removal of information about spurious relative motion of the instrument and the container or body employs a means to switch the resonant frequency of the instrument back and forth between a higher frequency and a lower frequency, where the auxiliary variable bias current source is frozen;

operation of the instrument at the higher frequency permits eddy current penetration to the target object enabling the instrument to deliver the composite signal, and operation at the lower frequency permits eddy currents only at the proximal surface of the container or body, so that the instrument output signal contains information only about the spurious relative motion of the instrument and the container or body, a sample and hold circuit causes the reading from the eddy current measurement apparatus at one frequency to exist while said apparatus is operating at the other frequency; and subtraction of the spurious relative motion signal from the composite signal occurs in a difference measuring circuit, whereby the instrument closed loop and open loop output signals contain information only about the internal properties and movement of a target object.

14. The system of claim 9, wherein: removal of information about spurious relative motion of the instrument and the container or body employs a means to switch the parallel resonant circuit of the instrument back and forth between a higher power level and a lower power level, where the auxiliary variable bias current source is frozen, operation of the parallel resonant circuit at the higher power permits eddy current penetration to the target object enabling the instrument to deliver the composite signal, and operation of the parallel resonant circuit at the lower power level permits eddy currents only at the proximal surface of the container or body, enabling the instrument to deliver the signal containing information about only about the spurious relative motion of the instrument and the container or body, a sample and hold circuit causes the reading from the eddy current measurement apparatus at one parallel resonant circuit power level to exist while the instrument is operating at the other power level; and subtraction of the spurious relative motion signal from the composite signal occurs in a difference measuring circuit, thereby leaving only information about the target object.

15. The system of claim 9: where the relative motion of the instrument and the container or body signal is caused mainly by accelerating motion of the instrument, the circuitry to provide the auxiliary current source with the relative motion of the instrument and the container or body signal, comprising an accelerometer, measuring an instantaneous acceleration of the instrument, driving a 1st time integrator circuit to provide a velocity signal from the accelerometer, driving a 2nd time integrator circuit to provide a position signal from the 1st time integrator circuit, and a means to initialize said integrator circuits whenever the instrument is touching the surface of the container or body, and additional accelerometer and integrator processing circuitry, where the 2nd time integrator feeds the auxiliary current source with the relative motion signal.

* * * * *